(12) United States Patent
Luca et al.

(10) Patent No.: US 11,993,645 B2
(45) Date of Patent: May 28, 2024

(54) COMPOSITIONS COMPRISING R-SPONDIN (RSPO) SURROGATE MOLECULES

(71) Applicant: The Board of Trustees of the Leland Stanford Junior University, Stanford, CA (US)

(72) Inventors: Vincent Christopher Luca, Menlo Park, CA (US); Kenan Christopher Garcia, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 54 days.

(21) Appl. No.: 16/476,501

(22) PCT Filed: Jan. 11, 2018

(86) PCT No.: PCT/US2018/013325
§ 371 (c)(1),
(2) Date: Jul. 8, 2019

(87) PCT Pub. No.: WO2018/132572
PCT Pub. Date: Jul. 19, 2018

(65) Prior Publication Data
US 2020/0024338 A1 Jan. 23, 2020

Related U.S. Application Data

(60) Provisional application No. 62/444,987, filed on Jan. 11, 2017.

(51) Int. Cl.
*C07K 16/18* (2006.01)
*A61K 38/00* (2006.01)
*C07K 14/54* (2006.01)
*C07K 14/55* (2006.01)

(52) U.S. Cl.
CPC .......... *C07K 16/18* (2013.01); *C07K 14/5406* (2013.01); *C07K 14/55* (2013.01); *A61K 38/00* (2013.01); *C07K 2317/622* (2013.01); *C07K 2317/77* (2013.01); *C07K 2319/21* (2013.01); *C07K 2319/81* (2013.01)

(58) Field of Classification Search
CPC .... C07K 16/18; C07K 16/28; C07K 16/3046; C07K 16/3069; C07K 16/40; C07K 14/5406; C07K 14/55; C07K 2317/31; C07K 2317/622; C07K 2317/77; C07K 2319/00; C07K 2319/21; C07K 2319/75; C07K 2319/81; A61K 38/00
See application file for complete search history.

(56) References Cited

U.S. PATENT DOCUMENTS

| | | | |
|---|---|---|---|
| 8,278,036 B2 | 10/2012 | Kariko et al. |
| 8,507,442 B2 | 8/2013 | Gurney et al. |
| 8,691,966 B2 | 4/2014 | Kariko et al. |
| 8,748,089 B2 | 6/2014 | Kariko et al. |
| 8,835,108 B2 | 9/2014 | Kariko et al. |
| 8,969,526 B2 | 3/2015 | Baehner et al. |
| 9,296,826 B2 | 3/2016 | Cong et al. |
| 9,771,427 B2 | 9/2017 | Hofer et al. |
| 2003/0044409 A1 | 3/2003 | Carson et al. |
| 2007/0244061 A1 | 10/2007 | Niehrs et al. |
| 2008/0038272 A1 | 2/2008 | Buehring et al. |
| 2008/0267955 A1 | 10/2008 | Schluesener et al. |
| 2010/0092457 A1 | 4/2010 | Aburatani et al. |
| 2010/0172895 A1 | 7/2010 | Boone et al. |
| 2013/0230521 A1 | 9/2013 | Nakamura et al. |
| 2014/0044713 A1 | 2/2014 | De Lau et al. |
| 2014/0105917 A1 | 4/2014 | Gurney |
| 2014/0328859 A1 | 11/2014 | Cong et al. |
| 2017/0158775 A1 | 6/2017 | Linden et al. |
| 2018/0066067 A1 | 3/2018 | Cong et al. |
| 2020/0048324 A1 | 2/2020 | Zhang et al. |

FOREIGN PATENT DOCUMENTS

| | | |
|---|---|---|
| EP | 2305274 | 4/2011 |
| EP | 2305274 A1 | 4/2011 |
| EP | 2331136 B1 | 1/2018 |
| WO | WO2008093646 | 7/2008 |
| WO | WO 2008/093646 A1 | 8/2008 |
| WO | WO 2010/092457 A1 | 8/2010 |
| WO | WO 2011/130624 A2 | 10/2011 |
| WO | WO 2012/045075 A1 | 4/2012 |
| WO | WO 2012/138453 A1 | 10/2012 |
| WO | WO2012140274 | 10/2012 |
| WO | 2013054307 | 4/2013 |

(Continued)

OTHER PUBLICATIONS

Jin YR and Yoon JK (Dec. 2012) Int J Biochem Cell Biol. 44(12):2278-2287. (doi: 10.1016/j.biocel.2012.09.006).*
Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983.*
Colman, PM (1994) Research in Immunology, Elsevier, NY, 145(1):33-36.*
Moon et al., Functional Modulation of Regulatory T Cells by IL-2. PLoS One. 2015, vol. 10(11):e0141864. PDF File: p. 1-13.

(Continued)

*Primary Examiner* — Robert S Landsman
(74) *Attorney, Agent, or Firm* — Pamela J. Sherwood; Bozicevic, Field & Francis LLP

(57) ABSTRACT

R-spondin (RSPO) surrogate compositions and methods for their use are provided. RSPO surrogates of the invention comprise (i) a specific binding domain for Ring Finger Protein 43 (RNF43) or Zinc and Ring Finger Protein 3 (ZNRF3) and (ii) a cell targeting domain More specifically, wherein the specific binding domain for RNF43 or ZNRF3 is an antibody fragment, and wherein the cell targeting domain is a cytokine.

10 Claims, 14 Drawing Sheets

Specification includes a Sequence Listing.

(56) References Cited

FOREIGN PATENT DOCUMENTS

| WO | WO 2013/052523 A1 | 4/2013 |
|----|----|----|
| WO | WO 2013/054307 A2 | 4/2013 |
| WO | WO 2013/071047 A1 | 5/2013 |
| WO | WO 2013/078199 A2 | 5/2013 |
| WO | WO2013130364 | 6/2013 |
| WO | WO 2013/130364 A1 | 9/2013 |
| WO | WO 2013/151666 A2 | 10/2013 |
| WO | WO 2014/023709 A1 | 2/2014 |
| WO | WO 2014/081507 A1 | 5/2014 |
| WO | WO 2014/093924 A1 | 6/2014 |
| WO | WO 2014/164253 A1 | 10/2014 |
| WO | 2015164392 | 10/2015 |
| WO | WO 2015/164392 A2 | 10/2015 |
| WO | WO 2016/040895 A1 | 3/2016 |
| WO | 2016073906 A2 | 5/2016 |
| WO | WO 2016/081640 A1 | 5/2016 |
| WO | 2017069628 | 4/2017 |
| WO | WO2017069628 | 4/2017 |
| WO | WO2017100467 | 6/2017 |
| WO | WO 2018/132572 A1 | 7/2018 |
| WO | WO 2018/140821 A1 | 8/2018 |
| WO | WO2018140821 | 8/2018 |
| WO | WO 2018/203567 A1 | 11/2018 |
| WO | WO 2018/215614 A1 | 11/2018 |
| WO | WO 2019/126398 A1 | 6/2019 |
| WO | WO 2020/250156 A1 | 12/2020 |

OTHER PUBLICATIONS

Keerthivasan et al., Wnt/Beta-catenin signaling in T-cells drives epigenetic imprinting of pro-inflammatory properties and promotes colitis and colon cancer. Sci Trans! Med. 2014, vol. 6(225): 225ra28. PDF File: p. 1-28.

Hao et al., ZNRF3 promotes Wnt receptor turnover in an R-spondin-sensitive manner. Nature.2012, vol. 485(7397), p. 195-200.

You et al., Wnt pathway-related gene expression in inflammatory bowel disease. Dig Dis Sci. 2008, vol. 53(4), p. 1013-9.

Pace et al., IL-4 Modulation of CD4+ CD25+ T Regulatory Cell-Mediated Suppression. J Immunol. 2005, vol. 174(12), p. 7645-53.

Eppink et al. (2015) "Abstract C21: Generation of Wnt- and mitogenic receptor binding bispecific antibodies to target cancer stem cells" Molecular Cancer Therapeutics,AACR-NCI-EORTC, vol. 14, XP055711 023,001: 1 0.1158/1535-7163.TARG-15-.

Clevers et al. (2014) "An integral program for tissue renewal and regeneration: Wnt signaling and stem cell control" Stem Cell Signaling, vol. 346 Issue 6205, 1248012-7.

D'Souza et al. (2015) "Asialoglycoprotein receptor mediated hepatocyte targeting—Strategies and applications" journal of Controlled Release 203 (2015) 126-139.

Gong et al. (2010) "Wnt Isoform-Specific Interactions with Coreceptor Specify Inhibition or Potentiation of Signaling by LRP6 Antibodies" PLos One, vol. 5, Issue. 9, e12682.

Hombach (2012) "Antibody-IL2 Fusion Proteins for Tumor Targeting" Methods in Molecular Biology, 611-626.

Janda et al. (2017) "Surrogate Wnt agonists that phenocopy canonical Wnt/(3-catenin signaling" 545(7653): 234—237.

Kim et al. (2008) "R-Spondin Family Members Regulate the Wnt Pathway by a Common Mechanism" Molecular Biology of the Cell, vol. 19, 2588-2596.

Witzigmann (2016) "Variable asialoglycoprotein receptor 1 expression in liver disease: Implications for therapeutic intervention" Hepatology Research 2016; 46: 686-696.

Xie et al. (2013) "Interaction with both ZNRF3 and LGR4 is required for the signaling activity of R-spondin" vol. 14, No. 12, pp. 1120-1126.

Eppink et al.(2015) "Abstract C21: Generation of Wnt-and mitogenic receptor binding bispecific antibodies to target cancer stem cells." Molecular Cancer Therapeutics 14(12) Supplement 2: C21-C21.

Apte et al. (Sep. 2009) Beta-catenin activation promotes liver regeneration after acetaminophen-induced injury. The American Journal of Pathology. 175(3):1056-1065. DOI: 10.2353/ajpath.2009.080976.

International Preliminary Report on Patentability for Application No. PCT/US2018/013325, mailed May 8, 2018, 19 pages.

International Search Report and Written Opinion for Application No. PCT/US2018/013325, mailed May 8, 2018, 19 pages.

Invitation to Pay Fees for Application No. PCT/US2018/013325, mailed Mar. 13, 2018, 3 pages.

Arumugam, T. et al. (Apr. 2015) "New Blocking Antibodies against Novel AGR2-C4.4A Pathway Reduce Growth and Metastasis of Pancreatic Tumors and Increase Survival in Mice" Molecular Cancer Therapeutics, 14(4):941-951.

Bhanot, P. et al. (Jul. 18, 1996) "A new member of the frizzled family from *Drosophila* functions as a Wingless receptor" Nature, 382:225-230.

Brott, B.K. and S.Y. Sokol (Sep. 2002) "Regulation of Wnt/LRP Signaling by Distinct Domains of Dickkopf Proteins" Mol Cell Biol, 22(17):6100-6110.

Clevers, H. et al. (Oct. 3, 2014) "An integral program for tissue renewal and regeneration: Wnt signaling and stem cell control" Science, 346(6205):1248012-1-1248012-7.

D'Souza, A.A. et al. (2015) "Asialoglycoprotein receptor mediated hepatocyte targeting—Strategies and applications", Journal of Controlled Release, 203:126-139.

Ettenberg S.A. et al. (Aug. 31, 2010) "Inhibition of tumorigenesis driven by different Wnt proteins requires blockade of distinct ligand-binding regions by LRP6 antibodies" Proc Natl Acad Sci USA, 107(35): 15473-15478.

GenBank Accession No. 001292473.1 "E3 ubiquitin-protein ligase RNF43 isoform 1 precursor [*Homo sapiens*]" Dec. 20, 2020, 4 pages.

GenBank Accession No. 001304871.1 "R-spondin-2 isoform 3 [*Homo sapiens*]" Feb. 23, 2021, 3 pages.

GenBank Accession No. AF177394.2 "*Homo sapiens* dickkopf-1 (DKK-1) mRNA, complete cds" Dec. 20, 2016, 2 pages.

GenBank Accession No. AF177395.1 "*Homo sapiens* dickkopf-2 (DKK-2) mRNA, complete cds" Oct. 16, 1999, 2 pages.

GenBank Accession No. NM_001466.4 "*Homo sapiens* frizzled class receptor 2 (FZD2), mRNA" Feb. 17, 2021, 5 pages.

GenBank Accession No. NM_002335.2 "*Homo sapiens* low density lipoprotein receptor-related protein 5 (LRP5), mRNA" May 3, 2014, 5 pages.

GenBank Accession No. NM_002336.2 "*Homo sapiens* LDL receptor related protein 6 (LRP6), mRNA" Oct. 20, 2018, 8 pages.

GenBank Accession No. NM_003391.3 "*Homo sapiens* Wnt family member 2 (WNT2), transcript variant 1, mRNA" Feb. 17, 2021, 4 pages.

GenBank Accession No. NM_003392.7 "*Homo sapiens* Wnt family member 5A (WNT5A), transcript variant 1, mRNA" Feb. 21, 2021, 5 pages.

GenBank Accession No. NM_003393.4 "*Homo sapiens* Wnt family member 8B (WNT8B), mRNA" Mar. 7, 2021, 4 pages.

GenBank Accession No. NM_003394.4 "*Homo sapiens* Wnt family member 10B (WNT10B), mRNA" Feb. 16, 2021, 4 pages.

GenBank Accession No. NM_003395.4 "*Homo sapiens* Wnt family member 9A (WNT9A), mRNA" Feb. 16, 2021, 4 pages.

GenBank Accession No. NM_003396.3 "*Homo sapiens* Wnt family member 9B (WNT9B), transcript variant 1, mRNA" Feb. 16, 2021, 4 pages.

GenBank Accession No. NM_003468.4 "*Homo sapiens* frizzled class receptor 5 (FZD5), mRNA" Feb. 18, 2021, 6 pages.

GenBank Accession No. NM_003505.2 "*Homo sapiens* frizzled class receptor 1 (FZD1), mRNA" Nov. 22, 2020, 4 pages.

GenBank Accession No. NM_003506.4 "*Homo sapiens* frizzled class receptor 6 (FZD6), transcript variant 1, mRNA" Feb. 16, 2021, 5 pages.

GenBank Accession No. NM_003507.2 "*Homo sapiens* frizzled class receptor 7 (FZD7), mRNA" Feb. 21, 2021, 5 pages.

GenBank Accession No. NM_003508.3 "*Homo sapiens* frizzled class receptor 9 (FZD9), mRNA" Feb. 17, 2021, 5 pages.

(56) References Cited

OTHER PUBLICATIONS

GenBank Accession No. NM_004185.4 "*Homo sapiens* Wnt family member 2B (WNT2B), transcript variant WNT-2B1, mRNA" Feb. 13, 2021, 4 pages.
GenBank Accession No. NM_004625.4 "*Homo sapiens* Wnt family member 7A (WNT7A), mRNA" Feb. 17, 2021, 5 pages.
GenBank Accession No. NM_004626.3 "*Homo sapiens* Wnt family member 11 (WNT11), mRNA" Feb. 17, 2021, 4 pages.
GenBank Accession No. NM_005430.4 "*Homo sapiens* Wnt family member 1 (WNT1), mRNA" Feb. 21, 2021, 4 pages.
GenBank Accession No. NM_006522.4 "*Homo sapiens* Wnt family member 6 (WNT6), mRNA" Feb. 16, 2021, 4 pages.
GenBank Accession No. NM_007197.4 "*Homo sapiens* frizzled class receptor 10 (FZD10), mRNA" Mar. 2, 2021, 5 pages.
GenBank Accession No. NM_012193.4 "*Homo sapiens* frizzled class receptor 4 (FZD4), mRNA" Mar. 16, 2021, 6 pages.
GenBank Accession No. NM_014419.4 "*Homo sapiens* dickkopf like acrosomal protein 1 (DKKL1), transcript variant 1, mRNA" Feb. 18, 2021, 4 pages.
GenBank Accession No. NM_014420.3 " Homo sapiens dickkopf WNT signaling pathway inhibitor 4 (DKK4), mRNA" Feb. 15, 2021, 4 pages.
GenBank Accession No. NM_014421.3 "*Homo sapiens* dickkopf WNT signaling pathway inhibitor 2 (DKK2), mRNA" Feb. 13, 2021, 4 pages.
GenBank Accession No. NM_015881.6 "*Homo sapiens* dickkopf WNT signaling pathway inhibitor 3 (DKK3), transcript variant 1, mRNA" Feb. 23, 2021, 5 pages.
GenBank Accession No. NM_016087.2 "*Homo sapiens* Wnt family member 16 (WNT16), transcript variant 2, mRNA" Jan. 18, 2021, 4 pages.
GenBank Accession No. NM_024494.2 "*Homo sapiens* Wnt family member 2B (WNT2B), transcript variant WNT-2B2, mRNAHomo sapiens Wnt family member 2B (WNT2B), transcript variant WNT-2B2, mRNA" Nov. 12, 2018, 4 pages.
GenBank Accession No. NM_025216.3 "*Homo sapiens* Wnt family member 10A (WNT10A), mRNA" Feb. 17, 2021, 4 pages.
GenBank Accession No. NM_030753.5 "*Homo sapiens* Wnt family member 3 (WNT3), mRNA" Mar. 2, 2021, 4 page.
GenBank Accession No. NM_030761.5 "*Homo sapiens* Wnt family member 4 (WNT4), mRNA" Feb. 15, 2021, 4 pages.
GenBank Accession No. NM_031866.3 "*Homo sapiens* frizzled class receptor 8 (FZD8), mRNA" Mar. 16, 2021, 5 pages.
GenBank Accession No. NM_032642.3 "*Homo sapiens* Wnt family member 5B (WNT5B), transcript variant 1, mRNA" Mar. 22, 2021, 4 pages.
GenBank Accession No. NM_033131.4 "*Homo sapiens* Wnt family member 3A (WNT3A), mRNA" Mar. 2, 2021, 4 pages.
GenBank Accession No. NM_058238.3 "*Homo sapiens* Wnt family member 7B (WNT7B), mRNA" Feb. 16, 2021, 4 pages.
GenBank Accession No. NM_058244.4 "*Homo sapiens* Wnt family member 8A (WNT8A), transcript variant 3, mRNA" Feb. 23, 2021, 4 pages.
GenBank Accession No. NM_145866.2 "*Homo sapiens* frizzled class receptor 3 (FZD3), transcript variant 2, mRNA" Feb. 21, 2021, 7 pages.
GenBank Accession No. NP_001193927.1 "E3 ubiquitin-protein ligase ZNRF3 isoform 1 precursor [*Homo sapiens*]" Feb. 17, 2021, 3 pages.
GenBank Accession No. NP_001662.1 "asialoglycoprotein receptor 1 isoform a [*Homo sapiens*]" Feb. 16, 2021, 3 pages.
GenBank Accession No. NP_036374.1 "dickkopf-related protein 1 precursor [*omo sapiens*]" Mar. 3, 2021, 3 pages.
GenBank Accession No. NP_055236.1 "dickkopf-related protein 2 precursor [*Homo sapiens*]" Feb. 13, 2021, 3 pages.
GenBank Accession No. NP_550436.1 "asialoglycoprotein receptor 2 isoform c [*Homo sapiens*]" Feb. 13, 2021, 3 pages.
GenBank Accession No. XP_005582755.1 "Predicted: asialoglycoprotein receptor 1 isoform X1 [Macaca fascicularis]" Jan. 25, 2016, 2 pages.

GenBank Accession No. XP_011523257.1 "E3 ubiquitin-protein ligase RNF43 isoform X1 [*Homo sapiens*]" Feb. 28, 2021, 2 pages.
Gong, Y. et al. (2010) "Wnt Isoform-Specific Interactions with Coreceptor Specify Inhibition or Potentiation of Signaling by LRP6 Antibodies" PLoS One, 5(9):e12682, doi:10.1371/journal.pone.0012682; 17 pages.
Heupel, W.-M. et al. (Aug. 1, 2008) "Pemphigus Vulgaris IgG Directly Inhibit Desmoglein 3-Mediated Transinteraction" Journal of Immunology, 181(3):1825-1834.
Ingham, P. W. (Oct. 1996) "Has the quest for a Wnt receptor finally frizzled out?" Trends Genet, 12(10):382-384.
International Search Report and Written Opinion for Application No. PCT/US2018/15595, mailed May 29, 2018, 12 pages.
Jacobsen, B. et al. (Oct. 1, 20140) "C4.4A as a biomarker in pulmonary adenocarcinoma and squamous cell carcinoma" World Journal of Clinical Oncology, 5(4):621-632.
Jacobsen, F.W. et al. (Feb. 3, 2017) "Engineering an IgG Scaffold Lacking Effector Function with Optimized Developability" J Biol Chem, 292:1865-1875.
Janda, C.Y. et al. (May 1, 20171) "Surrogate Wnt agonists that phenocopy canonical Wnt and ß-catenin signaling" Nature, 545(7653):234-237. HHS Public Access Author Manuscript, 35 pages.
Kim, K.- A. et al. (Jun. 2008) "R-Spondin Family Members Regulate the Wnt Pathway by a Common Mechanism" Mol Biol Cell, 19(6):2588-2596.
Knight, M.N. and K. Hankenson (2014) "R-spondins: Novel matricellular regulators of the skeleton" Matrix Biology, 37:157-161.
Krupnik, V.E. et al. (1999) "Functional and structural diversity of the human Dickkopf gene family" Gene, 238(2):301-313.
Li, L. et al. (Feb. 2, 20022) "Second Cysteine-rich Domain of Dickkopf-2 Activates Canonical Wnt Signaling Pathway via LRP-6 Independently of Dishevelled" J Biol Chem, 277(8):5977-5981.
Lo, M. et al. (Mar. 3, 2017) "Effector-attenuating Substitutions That Maintain Antibody Stability and Reduce Toxicity in Mice" J Biol Chem, 292:3900-3908.
Mannstadt, M. et al. (1999) "Receptors for PTH and PTHrP: their biological importance and functional properties" American Journal of Physiology, 277:F665-F675.
McMahon, A.P. (Jul. 1992) "The Wnt family of developmental regulators" Trends Genet, 8:236-242.
Miller, J.R. (Dec. 28, 2001) "The Wnts" Genome Biol, 3(1):3001.1-3001.15.
Ngora, H. et al. (Feb. 2012) "Membrane-Bound and Exosomal Metastasis-Associated C4.4A Promotes Migration by Associating with the α6β4 Integrin and MT1-MMP[1,2]" Neoplasia, 14(2):95-107.
Paret, B. et al. (Jul. 10, 2005) "Ly6 family member C4.4A binds laminins 1 and 5, associates with Galectin-3 and supports cell migration" International Journal of Cancer, 115(5): 724-733.
Skolnick et al. (2000) "From genes to protein structure and function: novel applications of computational approaches in the genomic era". Trends in Biotechnology, 18(1): 34-39.
Stockert, R.J. et al. (1991) "Structural Characteristics and Regulation of the Asialoglycoprotein Receptor" Targeted Diagnostics and Therapy 4:41-64.
Thomason, H.A. et al. (2010) "Desmosomes: adhesive strength and signalling in health and disease" Biochemical Journal, 429(3):419-433.
Witzigmann, D. et al. (2016) Variable asialoglycoprotein receptor 1 expression in liver disease: Implications fo therapeutic intervention. Hepatology Research. 46(7):686-696.
Worthen, C.A. and C.A. Enns (Mar. 6, 2014) "The role of hepatic transferring receptor 2 in the regulation of iron homeostasis in the body" Frontiers in Pharmacology, 5:34, 8 pages.
Xie, Y. et al. (Oct. 2013) "Interaction with both ZNRF3 and LGR4 is required for the signalling activity of R-spondin" EMBO Reports, 14(12):1120-1126.
Yan, H. et al. (Nov. 13, 2012) "Sodium taurocholate cotransporting polypeptide is a functional receptor for human hepatitis B and D virus" eLife, 1:e00049, http://dx.doi.org/10.7554/eLife.00049; 28 pages.

(56) References Cited

OTHER PUBLICATIONS

Yan, J-J. et al. (2015) "Active radar guides missile to its target: receptor-based targeted treatment of hepatocellular carcinoma by nanoparticulate systems" Tumor Biology, 36:55-67.

* cited by examiner

Z6 scFv

Z6 scFv

R5 scFv

R5 scFv

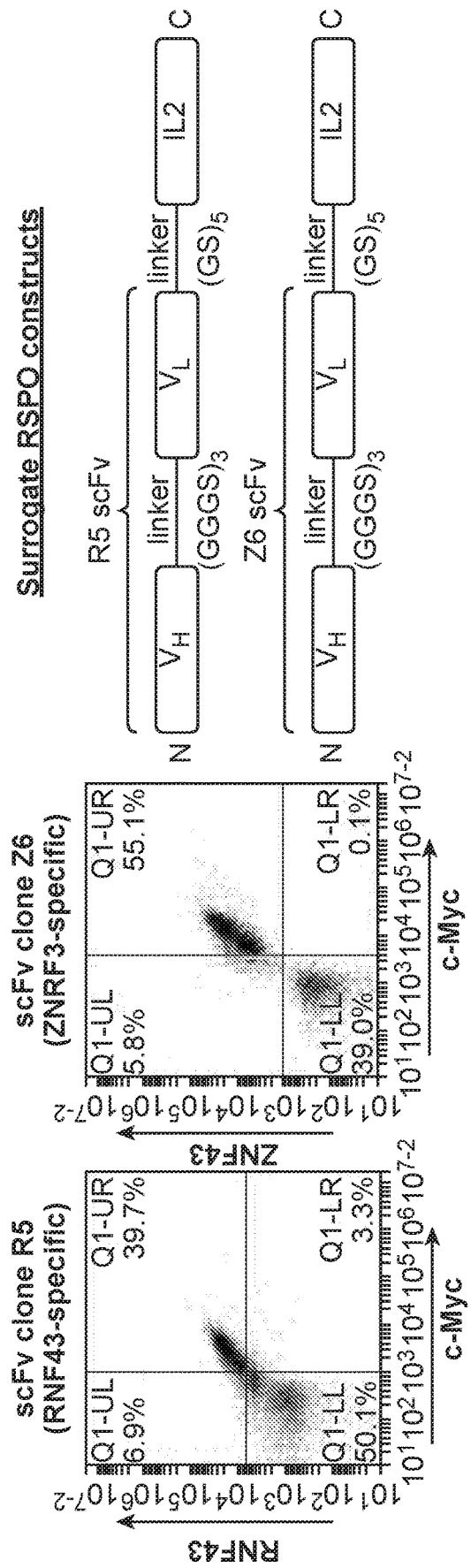
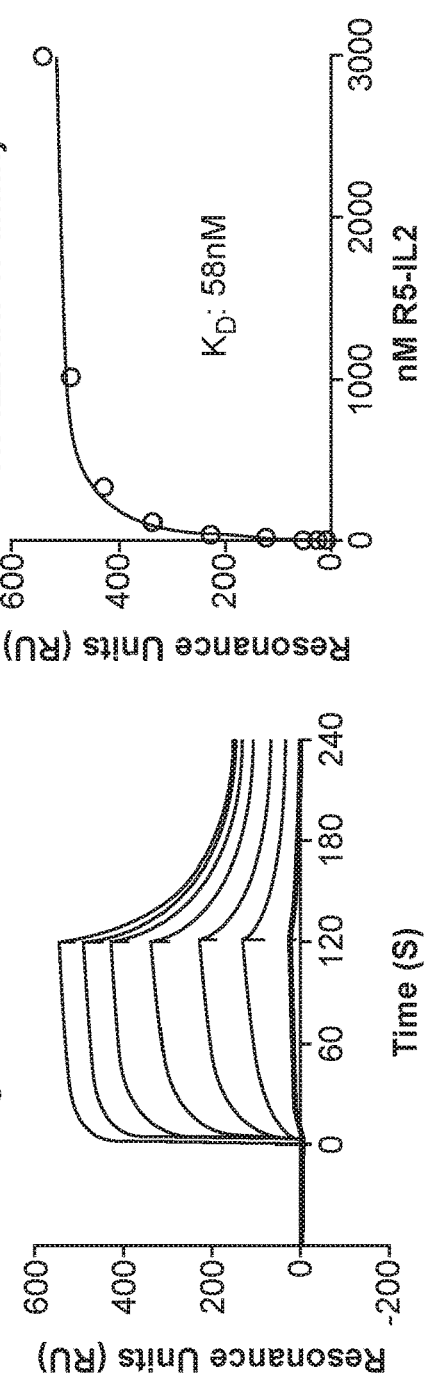
FIG. 8A
FIG. 8B
FIG. 8C

COMPOSITIONS COMPRISING R-SPONDIN (RSPO) SURROGATE MOLECULES

CROSS-REFERENCE TO RELATED APPLICATIONS

This application is a 371 of International Application PCT/US2018/013325, filed Jan. 11, 2018; and claims priority to U.S. Ser. No. 62/444,987, filed Jan. 11, 2017, now expired the contents of each of which is incorporated herein by reference.

BACKGROUND

The evolutionarily conserved Wnt signaling pathway plays critical roles in embryonic development and adult tissue homeostasis in all multicellular animals. Wnt proteins are secreted lipoglycoprotein ligands that control cell proliferation, migration, cell fate specification, and polarity formation. The canonical Wnt signaling cascade drives specific gene expression programs through regulating the stability of transcription cofactor β-catenin. Wnt proteins can also activate the β-catenin-independent Plana Cell Polarity (PCP) pathway to coordinate cell and tissue movements. The Frizzled (FZD) family of seven transmembrane-domain proteins serves as the core receptors of Wnt proteins, and they are required for both Wnt/β-catenin and Wnt/PCP signaling. Wnt proteins utilize different coreceptors to activate different downstream signaling pathways; Wnt proteins bind to coreceptor LRP5/6 to turn on the Wnt/β-catenin pathway, and they bind to coreceptor ROR1/2, RYK or PTK7 to initiate the Wnt/PCP pathway.

Ubiquitination-mediated turnover of Wnt receptors has emerged as a critical regulatory mechanism of Wnt pathway activity. Cell surface FZD levels are stabilized by UBPY/USP8 and USP6, suggesting that ubiquitination serves as an important regulatory mechanism underlying FZD lysosomal degradation. Cell surface transmembrane E3 ubiquitin ligase Zinc and Ring Finger 3 (ZNRF3) and its functional homolog Ring finger protein 43 (RNF43) act as negative feedback regulators of Wnt signaling. ZNRF3 and RNF43 inhibit Wnt/β-catenin signaling through promoting ubiquitination and subsequent internalization and degradation of Wnt receptor FZD and LRP6. Dishevelled (DVL) serves as a positive regulator of Wnt signaling through direct binding to FZD, and is an adaptor protein targeting ZNRF3/RNF43 to FZD to promote FZD ubiquitination and degradation.

R-spondin proteins (RSPO1-4) are secreted proteins that potently sensitize cells to Wnt/β-catenin signaling and Wnt/PCP signaling. All four RSPO proteins have similar domain structures with two N-terminal Furin domains and a C-terminal TSR domain. LGR4, LGR5 and LGR6 are high affinity receptors of RSPO; RSPO requires LGR4/5/6 to activate Wnt signaling, but it does not activate canonical GPCR signaling downstream of LGR4/5/6. RSPO potentiates Wnt signaling by simultaneously binding to the extracellular domains of ZNRF3/RNF43 and LGR4/5/6, inducing auto-ubiquitination and membrane clearance of ZNRF3/RNF43, resulting in increased cell surface level of FZD. Regulation of FZD turnover explains how RSPO can control both Wnt/β-catenin and Wnt/PCP signaling. RSPO binds to LGR4/5/6 through the Furin 1 and 2 domains, and binds to ZNRF3/RNF43 through the Furin 1 domain. RSPO needs to interact with both LGR4/5/6 and ZNRF3/RNF43 to be functional. Wnt stimulatory activities of different RSPO proteins are correlated with their binding affinities to ZNRF3 or RNF43.

A multitude of Wnt antagonists are secreted which function by blocking receptor access, sequestering Wnt ligands, or degrading Wnt. In contrast, RSPOs (Rspo1-4) are the sole secreted potentiators of Wnt signaling and have emerged as crucial regulators of stem cell maintenance in vivo and in vitro. RSPOs are being explored for many therapeutic applications ranging from bone regeneration to intestinal rejuvenation following chemotherapy. RSPOs are attractive drug candidates because they amplify existing Wnt signals while avoiding potential oncogenic or toxic off-target effects of global Wnt activation. However, RSPOs have limited clinical utility due to the requirement of LGR4/5/6 expression on the target cell type, and due to intrinsic cross-reactivity for RNF43/ZNRF3 and LGR4/5/6, and the broad tissue expression profiles of RNF43/ZNRF3 and LGR4/5/6 that would result in RSPO actions on many tissues, leading to pleiotropic effects and undesired toxicities.

Potential obstacles for the clinical use of Wnt agonists include diminished potency due to RNF43/ZNRF3-mediated antagonism and toxic off-target effects. Wnts are potent morphogens, and hyperactivation of the Wnt pathway has been implicated in the development of several human cancers. Development of surrogate molecules that provide RSPO activity that can be delivered in a cell and tissue-specific manner is therefore of great clinical interest.

SUMMARY

Compositions and methods of use thereof are provided of proteins that act as a surrogate RSPO (RSPO), which potentiate Wnt signaling on targeted cell types. In some embodiments the RSPO surrogate circumvents the requirement for expression of the RSPO cognate receptors LGR4, LGR5 or LGR6 for potentiation of Wnt signaling. In other embodiments the RSPO surrogate specifically targets one or more of LGR4, LGR5 or LGR6 for potentiation of Wnt signaling, thus providing enhanced selectivity for RSPO activity. In some other embodiments the RSPO surrogate specifically targets one or more cell surface receptors not including LGR4, LGR5 or LGR6 for potentiation of Wnt signaling, thus providing enhanced selectivity for RSPO activity.

An RSPO surrogate as used herein comprises (i) a specific binding domain for RNF43 or ZNRF3 and (ii) a cell targeting domain specific for a cell surface receptor expressed on a desired cell type to enable precise cell and tissue-specific Wnt potentiation. The domains may be directly joined, or may be separated by a linker, e.g. a polypeptide linker, or a non-peptidic linker, etc. The length of the linker, and therefore the spacing between the binding domains can be used to modulate the signal strength, and can be selected depending on the desired use of the RSPO surrogate. A polypeptide RSPO surrogate may be a single chain, dimer, or higher order multimer.

The RNF43 or ZNRF3 binding domain may be selected from any domain that binds RNF43 or ZNRF3 at high affinity, e.g. a Kd of not more than about $1 \times 10^{-6}$ M, not more about $1 \times 10^{-7}$ M, not more about $1 \times 10^{-9}$ M, not more about $1 \times 10^{-9}$ M, or not more about $1 \times 10^{-10}$ M. Suitable binding domains include, without limitation, de novo designed binding proteins, antibody derived binding proteins, e.g. scFv, Fab, etc. and other portions of antibodies that specifically bind to RNF43 or ZNRF3 proteins; nanobody derived binding domains; knottin-based engineered scaffolds; norrin and engineered binding fragments derived therefrom, naturally occurring binding domains, and the like. In some embodiments the specific binding domain for RNF43 or ZNRF3 is a binding fragment of RSPO, e.g. comprising, consisting or consisting essentially of an RSPO Furin 1 domain. A binding domain may be affinity selected to enhance binding to a desired protein or plurality of proteins.

The cell targeting domain or element may be selected from any domain that selectively binds to a cell surface protein, carbohydrate or lipid at high affinity, e.g. a $K_D$ of not more about $1\times10^{-7}$ M, not more than about $1\times10^{-8}$ M, not more than about $1\times10^{-9}$ M, not more than about $1\times10^{-10}$ M. Suitable cell targeting domains include, without limitation, de novo designed binding proteins, antibody derived binding proteins, e.g. scFv, Fab, etc. and other portions of antibodies that specifically bind to cell surface proteins, carbohydrates or lipids; nanobody derived binding domains; knottin-based engineered scaffolds; naturally occurring binding proteins or polypeptides, cytokines, growth factors, and the like.

In some embodiments the cell targeting domain is a cytokine or growth factor with a cognate receptor on the targeted cell. In some embodiments, the cytokine or growth factor contains a mutation, or mutations, that reduce its binding affinity for one or more of its cognate receptors. In some such embodiment, the surrogate RSPO may selectively target cells expressing individual receptor subunits of the multi-subunit cytokine receptor or growth factor receptor complexes.

In some embodiments, the targeting domain is a covalently linked small molecule, carbohydrate or nucleotide-derived molecule that binds to a cell surface protein, carbohydrate or lipid.

In some embodiments the cell targeting domain is an antibody or active fragment thereof with specificity for an antigen present on the targeted cell surface. In some such embodiments the antigen is one or more of LGR4, LGR5 or LGR6, e.g. an antibody that selectively binds to a single LGR protein, i.e. one of LGR4, LGR5 or LGR6. An LGR binding moiety may be selective for an LGR protein of interest, e.g. having a specificity for the desired LGR protein of at least 10-fold, 25-fold, 50-fold, 100-fold, 200-fold or more relative to other LGR proteins.

Contacting a targeted cell with an RSPO surrogate potentiates signaling in the Wnt pathway in the presence of Wnt, e.g. activity may be at least about 10%, at least about 20%, at least about 30%, at least about 40%, at least about 50%, at least about 60%, at least about 70%, at least about 80%, at least about 90%, and may be about a 2-fold, about a 3-fold, about a 4-fold, about a 5-fold or more increase in activity relative to the activity on the absence of the RSPO surrogate.

In some embodiments the linker is a rigid linker, in other embodiments the linker is a flexible linker. Where the linker is a peptide linker, it may be from about 1, 2, 3, 4, 5, 6, 7, 8, 9, 10, 11, 12, 13, 14, 15, 16, 17, 18, 19, 20 21, 22, 23, 24, 25, 26, 27, 28, 29, 30 or more amino acids in length, and is of sufficient length and amino acid composition to enforce the distance between binding domains. In some embodiments the linker comprises or consists of one or more glycine and/or serine residues.

A RSPO surrogate can be multimerized, e.g. through an Fc domain, by concatenation, coiled coils, polypeptide zippers, biotin/avidin or streptavidin multimerization, and the like. The RSPO surrogate can also be joined to a moiety such as PEG, Fc, etc. as known in the art to enhance stability in vivo.

Compositions of interest include, without limitation, an effective dose of a RSPO surrogate in a pharmaceutically acceptable excipient. Compositions may comprise additional agents, e.g. adjuvants and the like. RSPO surrogates may be produced synthetically; by various suitable recombinant methods, and the like, as known in the art.

In some aspects of the invention, a method is provided for potentiating Wnt signaling in a cell. In such methods, a cell expressing a frizzled receptor in the presence of a Wnt protein active on the Frizzled receptor is contacted with a concentration of an RSPO surrogate that is effective to increase signaling, e.g. to increase signaling by 25%, 50%, 75%, 90%, 95%, or more, relative to the signaling in the absence of the RSPO surrogate. Such signaling activation may induce proliferation, differentiation or a specific gene expression profile of/within the targeted cell, which cells include without limitation stem cells, or may otherwise enhance Wnt-signaling pathways in the targeted cell. In some methods, the cell is contacted in vitro. In other embodiments, the cell is contacted in vivo. Cells of interest include a wide variety of Fzd-receptor expressing cells, as are known in the art, for example skin cells, intestinal cells, osteoblasts, liver cells, chondrocytes, hair cells, stem cells, adult stem cells etc.

In some aspects of the invention, the RSPO surrogate is fused or bound to a Wnt agonist, a surrogate Wnt agonist, or natural Wnt protein to enhance Wnt signaling activity. In other embodiments enhanced Wnt signaling is achieved by co-administering the RSPO surrogate with a Wnt agonist, a surrogate Wnt agonist or natural Wnt protein.

In some aspects of the invention, a method is provided for treating or preventing a disease or disorder in a subject in need thereof, the method comprising providing to the subject an effective amount of an RSPO surrogate. In particular embodiments, the subject has a disease or disorder associated with reduced or naturally low Wnt signaling. In some aspects of the invention, a method is provided for enhancing wound healing and/or tissue generation in a subject in need thereof, the method comprising providing to the subject an effective amount of an RSPO surrogate.

In some aspects of the invention, an RSPO surrogate is targeted to selectively modulate the activity of regulatory T cells, which are suppressed by Wnt activation. In some such embodiments, the surrogate RSPO comprises IL-2 or an active fragment or derivative thereof as a targeting protein. IL-2 preferentially binds to regulatory T cells (T regs) over effector T cells. In related embodiments, an RSPO surrogate is targeted to cell type-specific surface markers on cells including, without limitation, macrophages, NK cells, dendritic cells, B cells, effector T cells and the like.

In some aspects of the invention, a method is provided for surrogate RSPO-mediated rejuvenation of intestinal stem cells, a process driven by three protein factors: RSPO, Epidermal Growth Factor (EGF) and Noggin. The surrogate RSPO may comprise an RNF43/ZNRF3 binding protein fused to EGF, which will circumvent the requirement for co-administration of RSPO and EGF by simultaneously activating RSPO and EGF signaling with a single agent.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIGS. 8A-8D. Characterization of RNF43- and ZNRF3-specific scFvs. (A) Flow cytometry dot plots depicting the binding of yeast-displayed R5 and Z6 scFvs to RNF43 and ZNRF3, respectively. R5- or Z6-expressing yeast were stained with 1 uM concentrations of RNF43 or ZNRF3 and surface expression was detected with an antibody to the c-Myc epitope. (B) Construct design for R5-IL2 and Z6-IL2 surrogate RSPOs. (C) & (D). SPR was used to measure the binding of R5-IL2 or Z6-IL2 to RNF43 and ZNRF3, respectively. Dissociation constants were obtained by fitting values to a 1:1 binding model.

DETAILED DESCRIPTION

Figure 1:
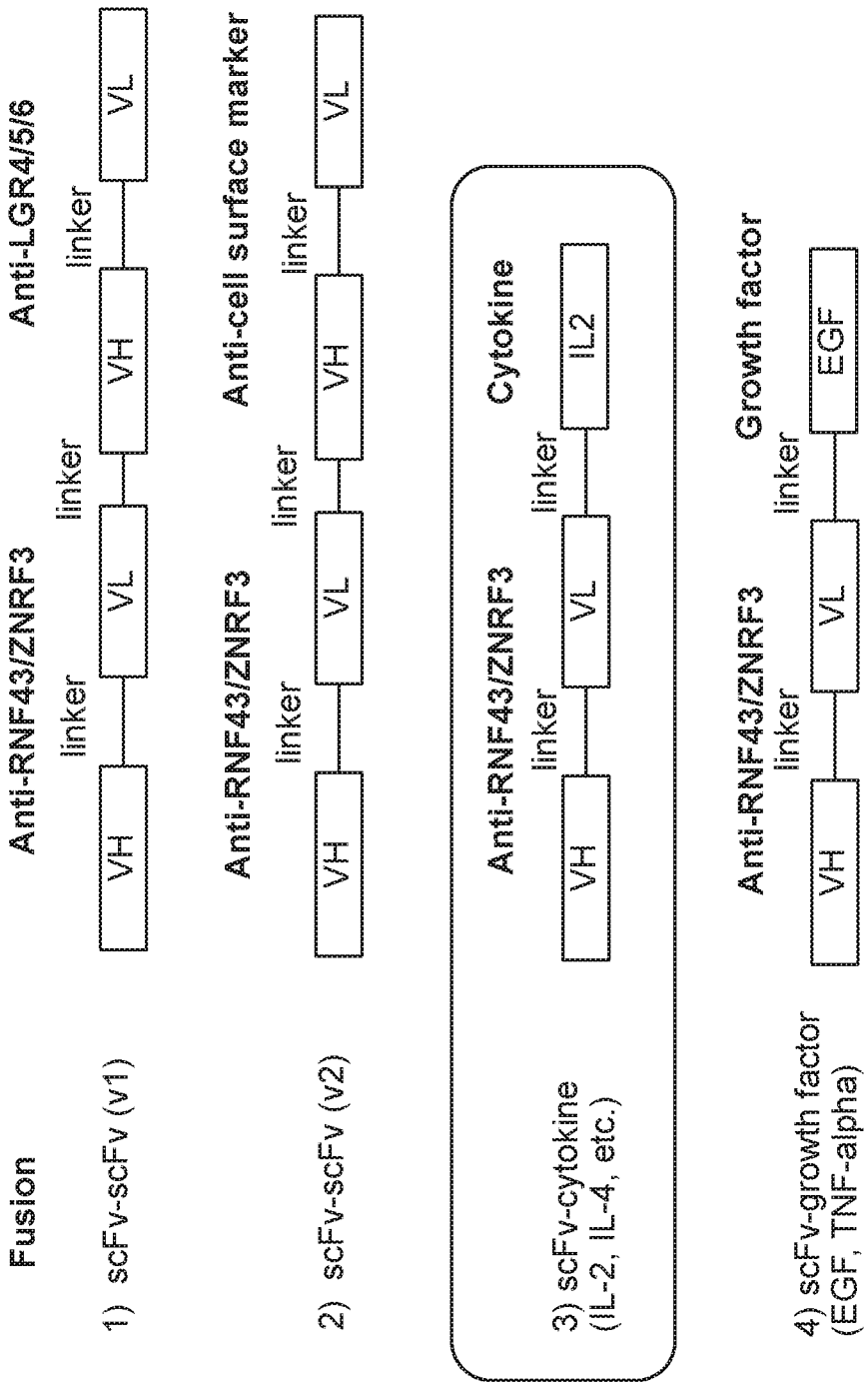
FIG. 1. Examples of surrogate RSPO proteins.
Figure 2:
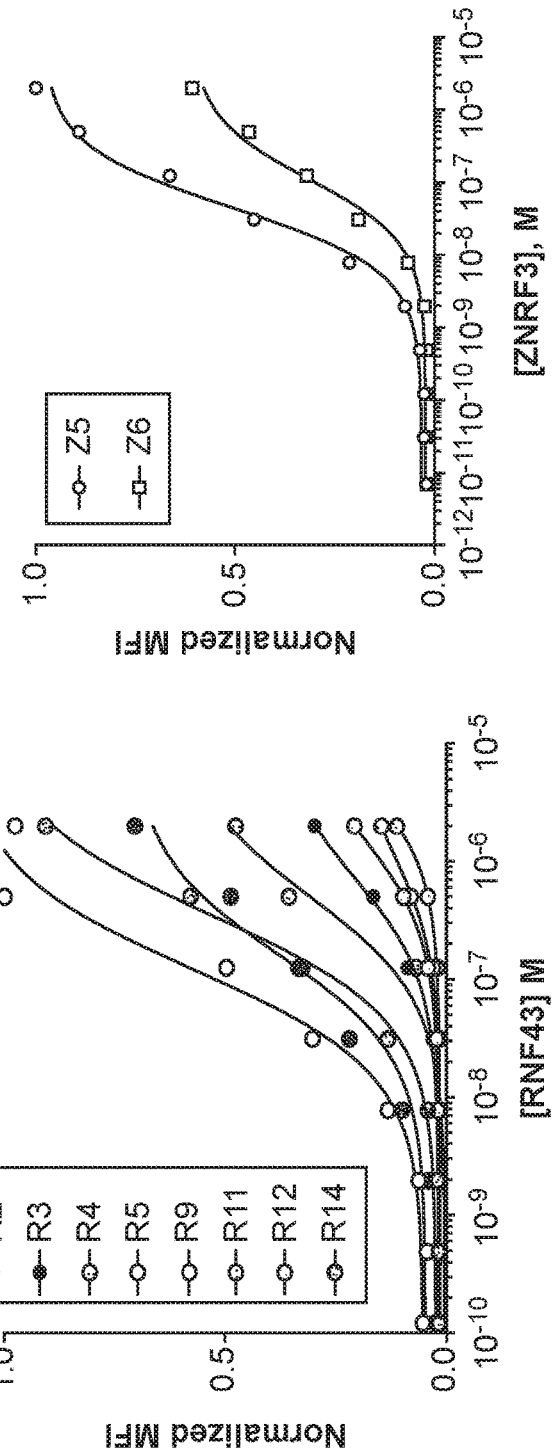
FIG. 2. Screening antibodies. To generate scFv antibody fragments specific for RNF43 or ZNRF3, binders were selected from a yeast display library of naïve human scFv constructs.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

By "comprising" it is meant that the recited elements are required in the composition/method/kit, but other elements may be included to form the composition/method/kit etc. within the scope of the claim. For example, a composition comprising a RSPO surrogate is a composition that may comprise other elements in addition to RSPO surrogate(s), e.g. functional moieties such as polypeptides, small molecules, or nucleic acids bound, e.g. covalently bound, to the RSPO surrogate; agents that promote the stability of the RSPO surrogate composition, agents that promote the solubility of the RSPO surrogate composition, adjuvants, etc. as will be readily understood in the art, with the exception of elements that are encompassed by any negative provisos.

By "consisting essentially of", it is meant a limitation of the scope of composition or method described to the specified materials or steps that do not materially affect the basic and novel characteristic(s) of the subject invention. For example, a RSPO surrogate "consisting essentially of" a disclosed sequence has the amino acid sequence of the disclosed sequence plus or minus about 5 amino acid residues at the boundaries of the sequence based upon the sequence from which it was derived, e.g. about 5 residues, 4 residues, 3 residues, 2 residues or about 1 residue less than the recited bounding amino acid residue, or about 1 residue, 2 residues, 3 residues, 4 residues, or 5 residues more than the recited bounding amino acid residue.

By "consisting of", it is meant the exclusion from the composition, method, or kit of any element, step, or ingredient not specified in the claim. For example, a RSPO surrogate "consisting of" a disclosed sequence consists only of the disclosed amino acid sequence.

The term "specific binding" refers to that binding which occurs between such paired species as enzyme/substrate, receptor/ligand, antibody/antigen, and lectin/carbohydrate which may be mediated by covalent or non-covalent interactions or a combination of covalent and non-covalent interactions. When the interaction of the two species produces a non-covalently bound complex, the binding that occurs is typically electrostatic, hydrogen-bonding, or the result of lipophilic interactions. Accordingly, "specific binding" occurs between a paired species where there is interaction between the two, which produces a bound complex having the characteristics of an antibody/antigen or ligand/receptor interaction. One may determine the biological activity of an RSPO surrogate in a composition by determining the level of activity in a functional assay after in vivo administration, e.g. accelerating bone regeneration, enhancing stem cell proliferation, etc., nuclear localization of β-catenin, increased transcription of Wnt-responsive genes; etc.

By "functional moiety" or "FM" it is meant a polypeptide, small molecule, carbohydrate or nucleic acid composition that confers a functional activity upon a composition. Examples of functional moieties include, without limitation, therapeutic moieties, binding moieties, and imaging moieties.

By "therapeutic moiety", or "TM", it is meant a polypeptide, small molecule or nucleic acid composition that confers a therapeutic activity upon a composition. Examples of therapeutic moieties include cytotoxins, e.g. small molecule compounds, protein toxins, and radiosensitizing moieties, i.e. radionuclides etc. that are intrinsically detrimental to a cell; agents that alter the activity of a cell, e.g. small molecules, peptide mimetics, cytokines, chemokines; and moieties that target a cell for ADCC or CDC-dependent death, e.g. the Fc component of immunoglobulin.

By an "imaging moiety", or "IM", it is meant a non-cytotoxic agent that can be used to locate and, optionally, visualize cells, e.g. cells that have been targeted by compositions of the subject application.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy may be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired, particularly humans.

General methods in molecular and cellular biochemistry can be found in such standard textbooks as Molecular Cloning: A Laboratory Manual, 3rd Ed. (Sambrook et al., CSH Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Polypeptides

As used herein, "protein" refers to any composition comprised of amino acids and recognized as a protein by those of skill in the art. The terms "protein," "peptide" and polypeptide are used interchangeably herein. Amino acids may be referred to by their complete names (e.g., alanine) or by the accepted one letter (e.g., A), or three letter (e.g., ala) abbreviations. Wherein a peptide is a portion of a protein, those skill in the art understand the use of the term in context. The term "protein" encompasses mature forms of proteins, as well as the pro- and prepro-forms of related proteins. Prepro forms of proteins comprise the mature form of the protein having a prosequence operably linked to the amino terminus of the protein, and a "pre-" or "signal" sequence operably linked to the amino terminus of the prosequence.

As used herein, "protein of interest," refers to a protein which is being analyzed, identified and/or modified. Naturally-occurring, as well as recombinant proteins, synthetically produced, variant and derivative proteins, all find use in the present invention.

As used herein, functionally similar proteins are considered to be "related proteins." In some embodiments, these proteins are derived from a different genus and/or species, including differences between classes of organisms (e.g., a bacterial protein and a fungal protein). In additional embodiments, related proteins are provided from the same species. Indeed, it is not intended that the present invention be limited to related proteins from any particular source(s).

As used herein, the term "derivative" refers to a protein which is derived from a precursor protein by addition of one or more amino acids to either or both the C- and N-terminal end(s), substitution of one or more amino acids at one or a number of different sites in the amino acid sequence, and/or deletion of one or more amino acids at either or both ends of the protein or at one or more sites in the amino acid sequence, and/or insertion of one or more amino acids at one or more sites in the amino acid sequence. The preparation of a protein derivative is preferably achieved by modifying a DNA sequence which encodes for the native protein, transformation of that DNA sequence into a suitable host, and expression of the modified DNA sequence to form the derivative protein.

One type of related (and derivative) proteins are "variant proteins." In preferred embodiments, variant proteins differ from a parent protein and one another by a small number of amino acid residues. The number of differing amino acid residues may be one or more, preferably 1, 2, 3, 4, 5, 10, 15, 20, 30, 40, 50, or more amino acid residues. In one preferred embodiment, the number of different amino acids between variants is between 1 and 10. In particularly preferred embodiments, related proteins and particularly variant proteins comprise at least 50%, 60%, 65%. 70%, 75%, 80%, 85%, 90%, 95%, 97%, 98%, or 99% amino acid sequence identity. Additionally, a related protein or a variant protein as used herein, refers to a protein that differs from another related protein or a parent protein in the number of prominent regions. For example, in some embodiments, variant proteins have 1, 2, 3, 4, 5, or 10 corresponding prominent regions that differ from the parent protein.

As used herein, "corresponding to," refers to a residue at the enumerated position in a protein or peptide, or a residue that is analogous, homologous, or equivalent to an enumerated residue in a protein or peptide. As used herein, "corresponding region" generally refers to an analogous position along related proteins or a parent protein.

As used herein, the term "analogous sequence" refers to a sequence within a protein that provides similar function, tertiary structure, and/or conserved residues as the protein of interest (i.e., typically the original protein of interest). In particularly preferred embodiments, the analogous sequence involves sequence(s) at or near an epitope. For example, in epitope regions that contain an alpha helix or a beta sheet structure, the replacement amino acids in the analogous sequence preferably maintain the same specific structure. The term also refers to nucleotide sequences, as well as amino acid sequences. In some embodiments, analogous sequences are developed such that the replacement amino acids show a similar function, the tertiary structure and/or conserved residues to the amino acids in the protein of interest at or near the epitope. Thus, where the epitope region contains, for example, an alpha-helix or a beta-sheet structure, the replacement amino acids preferably maintain that specific structure.

As used herein, "homologous protein" refers to a protein that has similar action, structure, antigenic, and/or immunogenic response as the protein of interest. It is not intended that a homolog and a protein of interest be necessarily related evolutionarily. Thus, it is intended that the term encompass the same functional protein obtained from different species.

As used herein, "wild-type" and "native" proteins are those found in nature. The terms "wild-type sequence," and "wild-type gene" are used interchangeably herein, to refer to a sequence that is native or naturally occurring in a host cell. In some embodiments, the wild-type sequence refers to a sequence of interest that is the starting point of a protein engineering project. The genes encoding the naturally-occurring (i.e., precursor) protein may be obtained in accord with the general methods known to those skilled in the art.

"Wnt gene product" or "Wnt polypeptide" when used herein encompass native sequence Wnt polypeptides, Wnt polypeptide variants, Wnt polypeptide fragments and chimeric Wnt polypeptides. In particular embodiments, a Wnt polypeptide is a native human full length mature Wnt protein.

For example, human native sequence Wnt proteins of interest in the present application include the following: Wnt-1 (GenBank Accession No. NM_005430); Wnt-2 (GenBank Accession No. NM_003391); Wnt-2B (Wnt-13) (GenBank Accession No. NM_004185 (isoform 1), NM_024494.2 (isoform 2)), Wnt-3 (RefSeq.: NM_030753), Wnt3a (GenBank Accession No. NM_033131), Wnt-4 (GenBank Accession No. NM_030761), Wnt-5A (GenBank Accession No. NM_003392), Wnt-5B (GenBank Accession No. NM_032642), Wnt-6 (GenBank Accession No. NM_006522), Wnt-7A (GenBank Accession No. NM_004625), Wnt-7B (GenBank Accession No. NM_058238), Wnt-8A (GenBank Accession No. NM_058244), Wnt-8B (GenBank Accession No. NM_003393), Wnt-9A (Wnt-14) (GenBank Accession No. NM_003395), Wnt-9B (Wnt-15) (GenBank Accession No. NM_003396), Wnt-10A (GenBank Accession No. NM_025216), Wnt-10B (GenBank Accession No. NM_003394), Wnt-11 (GenBank Accession No. NM_004626), Wnt-16 (GenBank Accession No. NM_016087)). Although each member has varying degrees of sequence identity with the family, all encode small (i.e., 39-46 kD), acylated, palmitoylated, secreted glycoproteins that contain 23-24 conserved cysteine residues whose spacing is highly conserved (McMahon, A P et al., Trends Genet. 1992; 8: 236-242; Miller, J R. Genome Biol. 2002; 3(1): 3001.1-3001.15). Other native sequence Wnt polypeptides of interest include orthologs of the above from any mammal, including domestic and farm animals, and zoo, laboratory or pet animals, such as dogs, cats, cattle, horses, sheep, pigs, goats, rabbits, rats, mice, frogs, zebra fish, fruit fly, worm, etc.

The RSPO family of proteins includes four members (Rspo1-4) that are conserved in vertebrates. The four RSPO proteins share ~40-60% pairwise sequence homology and adopt a common domain architecture that consists of an N-terminal secretory signal peptide sequence, two tandem furin-like cysteine-rich (Fu-CRD) domains, a thrombospondin type I repeat (TSP) domain, and a C-terminal basic amino acid-rich (BR) domain. Among the four subdomains, the two central tandem Fu-CRD domains have been demonstrated to be essential and sufficient for RSPO stimulation of Wnt signaling. RSPOs act immediately upstream of Wnt proteins. Accordingly, RSPO-driven Wnt activation is sensitive to the presence of the extracellular Wnt receptor inhibitor Dkk1.

The unique Wnt-enhancing ability of RSPOs, combined with their dynamic expression patterns in embryonic tissues, predicts important and pleiotropic roles for RSPOs during embryogenesis. Among other activities, RSPO1 is involved in sex determination. Expression of RSPO-2 has been reported in the oocytes of ovarian follicles. This oocyte-derived RSPO appeared to direct primary follicle development to the second stage in a paracrine matter. These observations are in line with the expression of multiple Wnt ligands and cognate Frizzled receptors in the ovary. RSPO-3 plays a dominant role during development of the placenta.

All four RSPOs bind with high affinity to all three LGR proteins. Sequences of exemplary human RSPO protein sequences are publicly available at Genbank, for example R-spondin-1 isoform 1 precursor [Homo sapiens], Accession: NP_001033722.1; R-spondin-1 isoform 2 [Homo sapiens], Accession: NP_001229838.1; R-spondin-1 isoform 3 precursor [Homo sapiens], Accession: NP_001229839.1; R-spondin-1 isoform X1 [Homo sapiens], Accession: XP_006710646.1; R-spondin-2 isoform X3 [Homo sapiens], Accession: XP_016868884.1; R-spondin-2 isoform 3 [Homo sapiens], Accession: NP_001304871.1; R-spondin-2 isoform X2 [Homo sapiens], Accession: XP_011515321.1; R-spondin-2 isoform X1 [Homo sapiens], Accession: XP_011515320.1; R-spondin-2 isoform 2 precursor [Homo sapiens], Accession: NP_001269792.1; R-spondin-2 isoform 1 precursor [Homo sapiens], Accession: NP_848660.3 GI: 222446611; R-spondin-3 precursor [Homo sapiens], Accession: NP_116173.2; R-spondin-4 isoform 1 precursor [Homo sapiens], Accession: NP_001025042.2; R-spondin-4 isoform 2 precursor [Homo sapiens], Accession: NP_001035096.1.

E3 ubiquitin ligases involved in Wnt-LGR/RSPO signaling. RNF43 and ZNRF3 are two highly homologous Wnt target genes and are RING domain E3 ligases. Both proteins show, in their basic structure and sequence, relatedness to Grail (Rnf128), a single-pass transmembrane E3 ligase with extracellular PA domain. RNF43 and ZNRF3 specifically mediate multiubiquitination of lysines in the cytoplasmic loops of the 7TM domain of Frizzleds. This results in the rapid endocytosis of Wnt receptors and their destruction in lysosomes. Since RNF43 and ZNRF3 are encoded by Wnt target genes, they may function as negative feedback regulators of Wnt receptor expression. Loss of expression of these two E3 ligases is predicted to result in hyperresponsiveness to endogenous Wnt signals. Indeed, mutations in RNF43 are seen in some human colon cancer cell lines and a variety of human tumor types affecting the bile duct, pancreas, and ovary. RNF43/ZNRF3-mediated membrane clearance of Wnt receptors is reversed upon addition of RSPO. RSPO-LGR complexes neutralize RNF43/ZNRF3, allowing for the persistence of surface Frizzled receptors and boosting of Wnt signal strength.

Sequences of exemplary human E3 ubiquitin ligases are publicly available at Genbank, for example E3 ubiquitin-protein ligase RNF43 isoform 1 precursor [Homo sapiens], Accession: NP_001292473.1 or NP_060233.3; E3 ubiquitin-protein ligase RNF43 isoform 2 [Homo sapiens], Accession: NP_001292474.1; E3 ubiquitin-protein ligase RNF43 isoform X1 [Homo sapiens], Accession: XP_016880289.1 or XP_011523257.1; E3 ubiquitin-protein ligase RNF43 isoform X2 [Homo sapiens], Accession: XP_011523258.1; E3 ubiquitin-protein ligase ZNRF3 isoform 1 precursor [Homo sapiens], Accession: NP_001193927.1; E3 ubiquitin-protein ligase ZNRF3 isoform 2 [Homo sapiens], Accession: NP_115549.2.

Antibodies that specifically bind to RNF43 and ZNRF3 are known in the art and are commercially available, or can be generated de novo. RNF43 and ZNRF3 or fragments thereof can be used as an immunogen or in screening assays to develop an antibody, for example by screening a library, immunization of an animal, etc., as known in the art. Examples of known antibodies include, without limitation, those described herein.

An RNF43/ZNRF3 binding domain may be affinity selected to enhance binding to a desired protein. Methods of affinity selection for this purpose may optionally utilize one or more rounds of selection by introducing targeted amino acid changes and generating a library of candidate coding sequences, transforming a population of cells with the candidate coding sequence, e.g. into yeast cells, selecting (for example using paramagnetic microbeads) for the desired specificity. Typically multiple rounds of selection will be performed, and the resulting vectors sequenced and used as the basis for protein engineering.

Figure 3:
FIG. 3. A candidate surrogate RSPO was generated by fusing the Z6 scFv, which specifically binds to ZNRF3, to human IL2 using linkers (SEQ ID NO:18) as shown.
Figure 4:
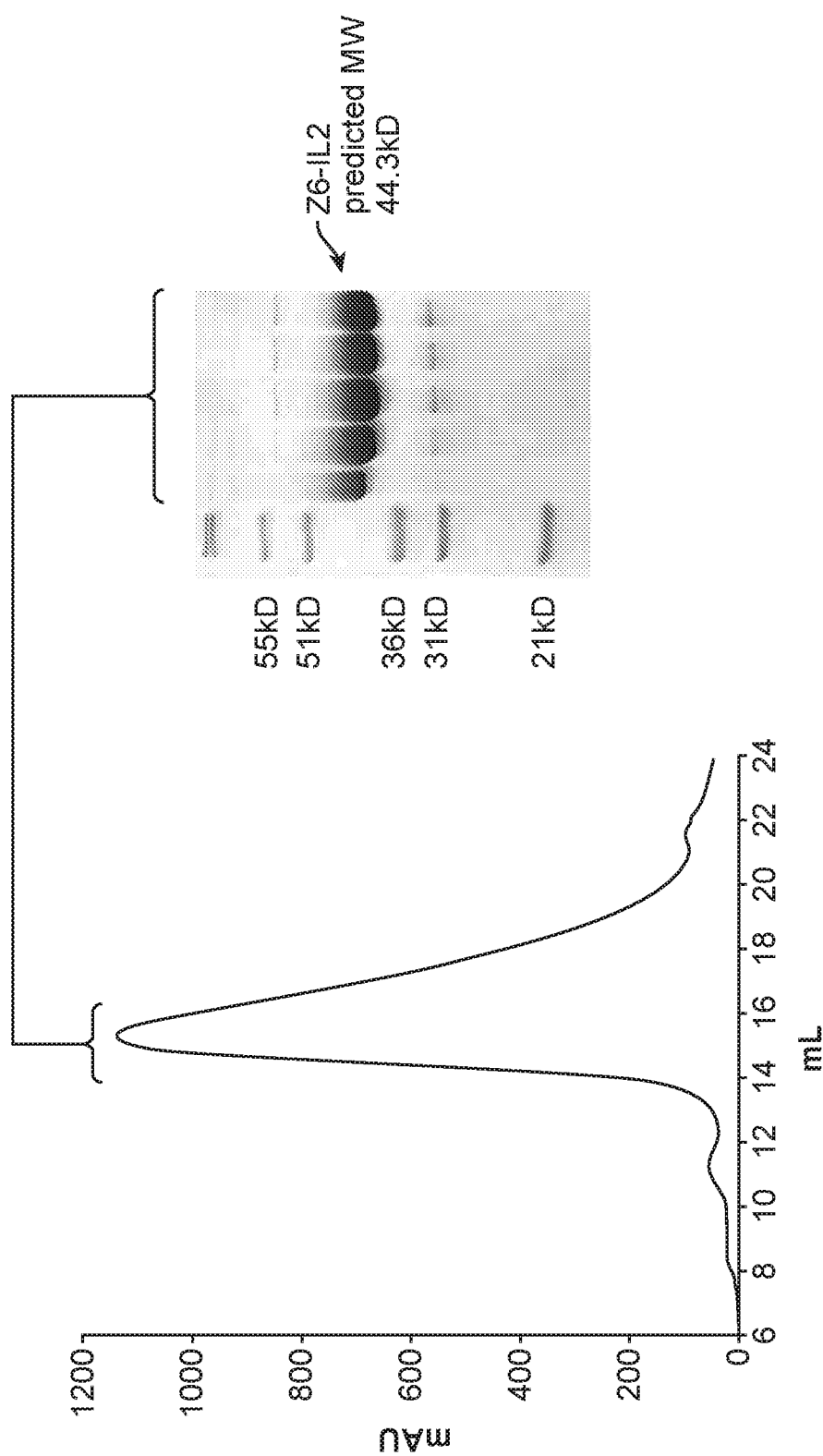
FIG. 4. Z6-IL2 fusion was expressed in insect cells and purified by nickel and gel filtration chromatography. Z6-IL2 elutes as a monodisperse peak from the gel filtration column, indicating that the protein is not aggregated and has favorable biochemical behavior.
Figure 5:
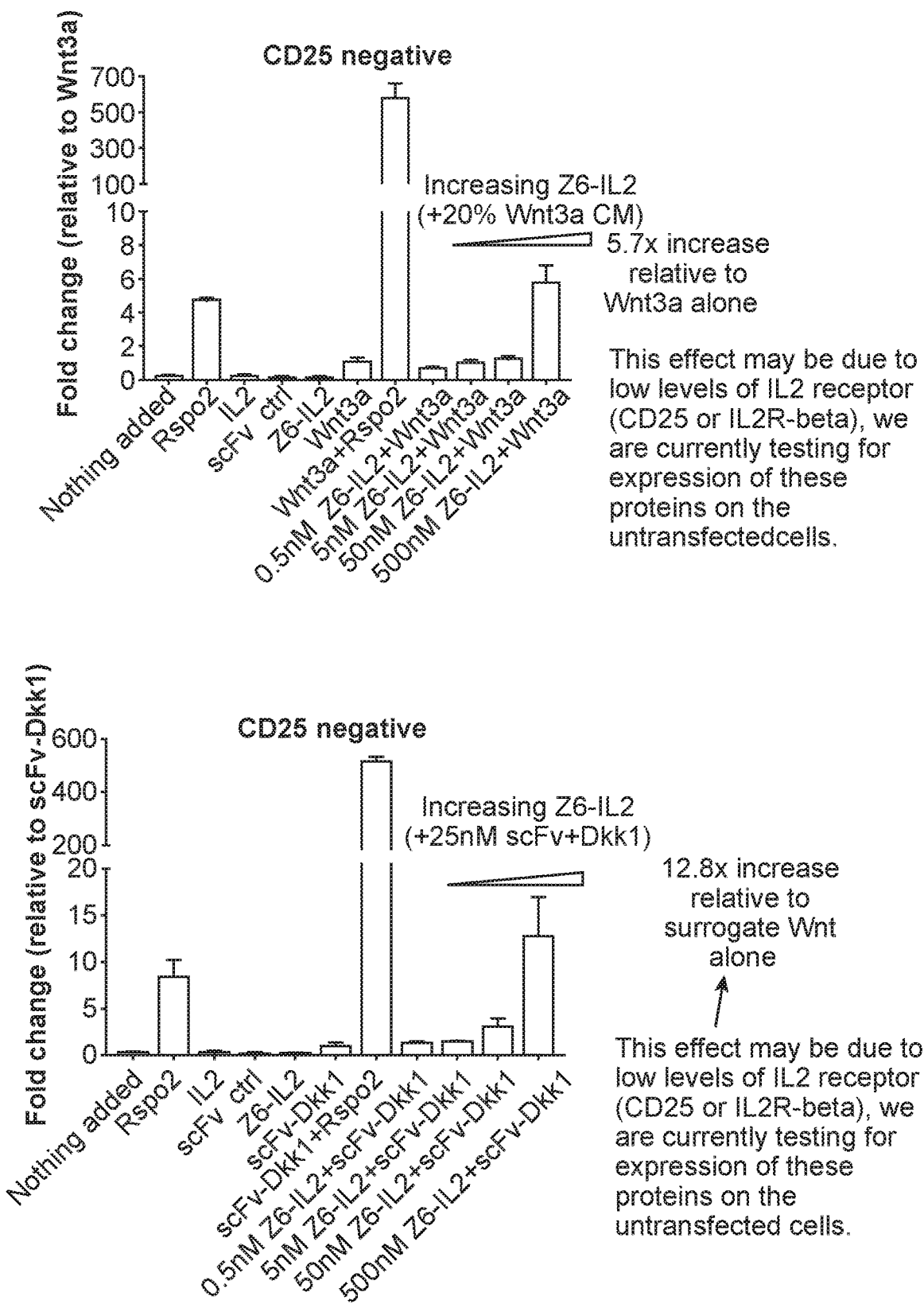
FIG. 5. Biological effects of surrogate RSPO.
Figure 5:
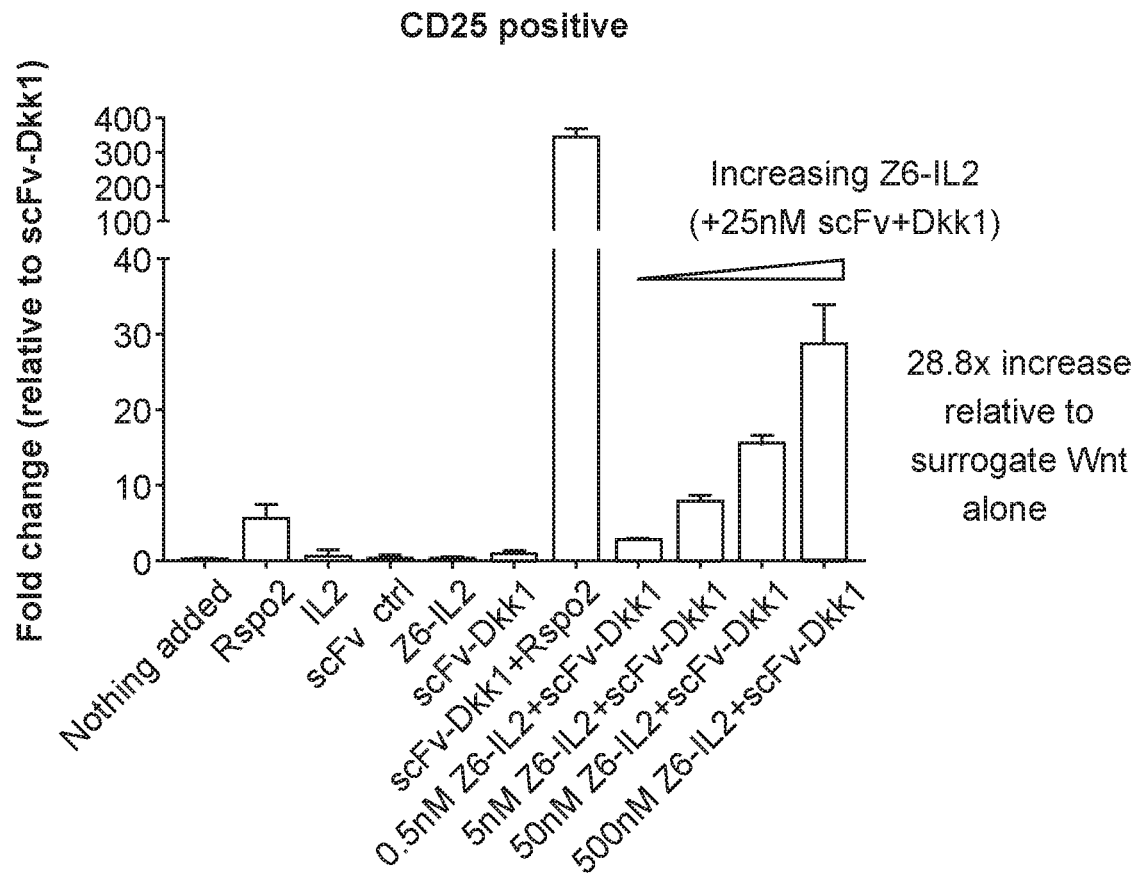
Figure 6:
FIG. 6. Further surrogate RSPO constructs.
Figure 6:
Figure 6:
Figure 6:

In certain embodiments, the RNF43/ZNRF3 binding domain comprises the six CDR regions of the scFv antibody exemplified herein, and as shown in FIG. 3.

In other embodiments, the binding domain comprises a variable region sequence, or the CDRs thereof, from any of a number of RNF43/ZNRF3 specific antibodies, which are known in the art and are commercially available, or can be generated de novo. RNF43/ZNRF3 can be used as an immunogen or in screening assays to develop an antibody.

Group B, leucine-rich repeat G-protein-coupled receptors (LGR4, 5, 6) are a unique class of GPCRs characterized by a large extracellular domain (ectodomain) that harbors 17 copies of leucine-rich repeat (LRR). LRRs are structural motifs that consist of a conserved 11-residue sequence rich in hydrophobic amino acids; often leucines are at defined positions (LxxLxLxxNxL, where x is any amino acid). The tertiary fold of a string of LRR repeats is known as an α/β horseshoe. The extracellular domain links ligand binding to modulation of downstream LGR intracellular signaling pathways. The 17 LRR repeats of the LGR4-6 receptors are flanked by the N-terminal cysteine-rich LRRNT region and the C-terminal cysteine-rich LRRCT region. The ectodomain mediates ligand binding to modulate downstream intracellular signaling pathways. LGR4-6 share ~50% sequence identity and play key roles in stem cell development, being found on a variety of epithelial stem cells, e.g. hair, skin, intestine, breast tissue, etc. LGR5 is also strongly expressed in cancers of the ovary, liver, and lung.

Sequences of exemplary human LGR protein sequences are publicly available at Genbank, for example leucine-rich repeat-containing G-protein coupled receptor 4 isoform 1 precursor [Homo sapiens], Accession: NP_060960.2; leucine-rich repeat-containing G-protein coupled receptor 4 isoform 2 precursor [Homo sapiens], Accession: NP_001333361.1; leucine-rich repeat-containing G-protein coupled receptor 5 isoform 3 precursor [Homo sapiens], Accession: NP_001264156.1; leucine-rich repeat-containing G-protein coupled receptor 5 isoform 2 precursor [Homo sapiens], Accession: NP_001264155.1; leucine-rich repeat-containing G-protein coupled receptor 5 isoform 1 precursor [Homo sapiens], Accession: NP_003658.1; leucine-rich repeat-containing G-protein coupled receptor 6 isoform 3 [Homo sapiens], Accession: NP_001017404.1; leucine-rich repeat-containing G-protein coupled receptor 6 isoform 2 [Homo sapiens], Accession: NP_067649.2; leucine-rich repeat-containing G-protein coupled receptor 6 isoform 1 precursor [Homo sapiens], Accession: NP_001017403.1.

The term "cytokine" or "cytokines" as used herein refers to the general class of biological molecules which effect/affect cells of the immune system. The definition is meant to include, but is not limited to, those biological molecules that act locally or may circulate in the blood, and which, when used in the compositions or methods described herein can target the RSPO surrogate to a cell of interest. Exemplary cytokines for use cell targeting include but are not limited to interferon-alpha (IFN-α), interferon-beta (IFN-β), and interferon-gamma (IFN-γ), interleukins (e.g., IL-1 to IL-29, in particular, IL-2, IL-5, IL-6, IL-7, IL-10, IL-12, IL-15 and IL-18), tumor necrosis factors (e.g., TNF-alpha and TNF-beta), erythropoietin (EPO), MIP3a, monocyte chemotactic protein (MCP)-1, intracellular adhesion molecule (ICAM), macrophage colony stimulating factor (M-CSF), granulocyte colony stimulating factor (G-CSF) and granulocyte-macrophage colony stimulating factor (GM-CSF). It is intended that the term also encompass modified cytokine molecules (i.e., "variant cytokines"), including those with substitutions, deletions, and/or additions to the cytokine receptor amino acid and/or nucleic acid sequence. Thus, it is intended that the term encompass wild-type, as well as recombinant, synthetically-produced, and variant cytokine receptors. As used herein, "cytokine receptor" refers to receptor molecules that recognize and bind to cytokines.

As an alternative to a cytokine, a number of domains or molecules can be used to target the RSPO surrogate to a cell, including any growth factor with a specific cell surface receptor, cell surface antigens to which an antibody or analog there can be derived, small molecules, nucleotides, hormones or carbohydrates that bind to cell surface receptors, and the like.

Binding domains may also include derivatives, variants, and biologically active fragments of polypeptides described above. A "variant" polypeptide means a biologically active polypeptide as defined below having less than 100% sequence identity with a provided sequence. Such variants include polypeptides comprising one or more amino acid modifications, e.g., insertions, deletions or substitutions, as compared to the provided sequence, e.g., wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%.

A "functional derivative" of a sequence is a compound having a qualitative biological property in common with an initial sequence. "Functional derivatives" include, but are not limited to, fragments of a sequence and derivatives of a sequence, provided that they have a biological activity in common. The term "derivative" encompasses both amino acid sequence variants of polypeptide and covalent modifications thereof.

RSPO surrogates for use in the subject compositions and methods may be modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The RSPO surrogates may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like. If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

Linker. The RNF43/ZNRF3 binding domain and the cell targeting domain may be separated by a linker, e.g. a polypeptide linker, or a non-peptidic linker, etc. The amino acid linkers that join domains can play an important role in the structure and function of multi-domain proteins. There are numerous examples of proteins whose catalytic activity requires proper linker composition. In general, altering the length of linkers connecting domains has been shown to affect protein stability, folding rates and domain-domain orientation (see George and Hering (2003) Prot. Eng. 15:871-879). The length of the linker in the RSPO surrogate, and therefore the spacing between the binding domains, can be used to modulate the signal strength of the RSPO surrogate, and can be selected depending on the desired use of the RSPO surrogate. The enforced distance between binding domains of a RSPO surrogate can vary, but in certain embodiments may be less than about 100 angstroms, less than about 90 angstroms, less than about 80 angstroms, less than about 70 angstroms, less than about 60 angstroms, less than about 50 angstroms.

In some embodiments the linker is a rigid linker, in other embodiments the linker is a flexible linker. In some embodiments, the linker moiety is a peptide linker. In some embodiments, the peptide linker comprises 2 to 100 amino acids. In some embodiments, the peptide linker comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 but no greater than 100 amino acids. In some embodiments, the peptide linker is between 5 to 75, 5 to 50, 5 to 25, 5 to 20, 5 to 15, 5 to 10 or 5 to 9 amino acids in length. Exemplary linkers include linear peptides having at least two amino acid residues such as Gly-Gly, Gly-Ala-Gly, Gly-Pro-Ala, Gly-Gly-Gly-Gly-Ser. Suitable linear peptides include poly glycine, polyserine, polyproline, polyalanine and oligopeptides consisting of alanyl and/or serinyl and/or prolinyl and/or glycyl amino acid residues. In some embodiments, the peptide linker comprises the amino acid sequence selected from the group consisting of $Gly_9$, $Glu_9$, $Ser_9$, $Gly_5$-Cys-$Pro_2$-Cys, $(Gly_4$-Ser$)_3$, Ser-Cys-Val-Pro-Leu-Met-Arg-Cys-Gly-Gly-Cys-Cys-Asn, Pro-Ser-Cys-Val-Pro-Leu-Met-Arg-Cys-Gly-Gly-Cys-Cys-Asn, Gly-Asp-Leu-Ile-Tyr-Arg-Asn-Gln-Lys, and $Gly_9$-Pro-Ser-Cys-Val-Pro-Leu-Met-Arg-Cys-Gly-Gly-Cys-Cys-Asn. In one embodiment a linker comprises the amino acid sequence GSTSGSGKSSEGKG, or (GGGGS)n, where n is 1, 2, 3, 4, 5, etc.; however many such linkers are known and used in the art and may serve this purpose.

RSPO surrogates can be provided in single-chain form, which means that the binding domains are linked by peptide bonds through a linker peptide. In other embodiments, the binding domains are individual peptides and can be joined through a non-peptidic linker.

Chemical groups that find use in linking binding domains include carbamate; amide (amine plus carboxylic acid); ester (alcohol plus carboxylic acid), thioether (haloalkane plus sulfhydryl; maleimide plus sulfhydryl), Schiff's base (amine plus aldehyde), urea (amine plus isocyanate), thiourea (amine plus isothiocyanate), sulfonamide (amine plus sulfonyl chloride), disulfide; hyrodrazone, lipids, and the like, as known in the art.

The linkage between binding domains may comprise spacers, e.g. alkyl spacers, which may be linear or branched, usually linear, and may include one or more unsaturated bonds; usually having from one to about 300 carbon atoms; more usually from about one to 25 carbon atoms; and may be from about three to 12 carbon atoms. Spacers of this type may also comprise heteroatoms or functional groups, including amines, ethers, phosphodiesters, and the like. Specific structures of interest include: $(CH_2CH_2O)n$ where n is from 1 to about 12; $(CH_2CH_2NH)n$, where n is from 1 to about 12; $[(CH_2)n(C{=}O)NH(CH_2)_m]_z$, where n and m are from 1 to about 6, and z is from 1 to about 10; $[(CH_2)nOPO_3(CH_2)_m]_z$ where n and m are from 1 to about 6, and z is from 1 to about 10. Such linkers may include polyethylene glycol, which may be linear or branched.

The binding domains may be joined through a homo- or heterobifunctional linker having a group at one end capable of forming a stable linkage to the hydrophilic head group, and a group at the opposite end capable of forming a stable linkage to the targeting moiety. Illustrative entities include: azidobenzoyl hydrazide, N-[4-(p-azidosalicylamino)butyl]-3'-[2'-pyridyldithio]propionamide), bis-sulfosuccinimidyl suberate, dimethyladipimidate, disuccinimidyltartrate, N-γ-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl] aminobenzoate, glutaraldehyde, NHS-PEG-MAL; succinimidyl 4-[N-maleimidomethyl]cyclohexane-1-carboxylate; 3-(2-pyridyldithio)propionic acid N-hydroxysuccinimide ester (SPDP); N, N'-(1,3-phenylene) bismaleimide; N, N'-ethylene-bis-(iodoacetamide); or 4-(N-maleimidomethyl)-cyclohexane-1-carboxylic acid N-hydroxysuccinimide ester (SMCC); m-maleimidobenzoyl-N-hydroxysuccinimide ester (MBS), and succinimide 4-(p-maleimidophenyl) butyrate (SMPB), an extended chain analog of MBS. The succinimidyl group of these cross-linkers reacts with a primary amine, and the thiol-reactive maleimide forms a covalent bond with the thiol of a cysteine residue.

Other reagents useful for this purpose include: p,p'-difluoro-m,m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); disdiazobenzidine (which reacts primarily with tyrosine and histidine); O-benzotriazolyloxy tetramethuluronium hexafluorophosphate (HATU), dicyclohexyl carbodiimde, bromo-tris (pyrrolidino) phosphonium bromide (PyBroP); N,N-dimethylamino pyridine (DMAP); 4-pyrrolidino pyridine; N-hydroxy benzotriazole; and the like. Homobifunctional cross-linking reagents include bis-maleimidohexane ("BMH").

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure.

The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation.

Any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, antibody sequence elements are humanized, primatized, chimeric, etc., as is known in the art.

Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgG, IgE and IgM, bi- or multi-specific antibodies (e.g., Zybodies®, etc.), single chain Fvs, Fabs, Small Modular ImmunoPharmaceuticals ("SMIPs™"), single chain or Tandem diabodies (TandAb®), VHHs, Anticalins®, Nanobodies®, minibodies, BiTE®s, ankyrin repeat proteins or DARPINs®, Avimers®, a DART, a TCR-like antibody, Adnectins®, Affilins®, Trans-bodies®, Affibodies®, a TrimerX®, MicroProteins, Fynomers®, Centyrins®, and a KALBITOR®. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc.], or other pendant group [e.g., poly-ethylene glycol, etc.]

In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain, which is homologous or largely homologous to an immunoglobulin-binding domain.

Expression construct: In the present methods, an RSPO surrogate may be produced by recombinant methods. Amino acid sequence variants of are prepared by introducing appropriate nucleotide changes into the DNA coding sequence. Such variants represent insertions, substitutions, and/or specified deletions of, residues within or at one or both of the ends of the amino acid sequence. Any combination of insertion, substitution, and/or specified deletion is made to arrive at the final construct, provided that the final construct possesses the desired biological activity as defined herein. The amino acid changes also may alter post-translational processes of the polypeptide, such as changing the number or position of glycosylation sites, altering the membrane anchoring characteristics, and/or altering the cellular location by inserting, deleting, or otherwise affecting the leader sequence of a polypeptide.

The nucleic acid encoding the surrogate can be inserted into a replicable vector for expression. Many such vectors are available. The vector components generally include, but are not limited to, one or more of the following: an origin of replication, one or more marker genes, an enhancer element, a promoter, and a transcription termination sequence.

Expression vectors will contain a promoter that is recognized by the host organism and is operably linked to the surrogate coding sequence. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature.

Expression vectors used in eukaryotic host cells (yeast, fungi, insect, plant, animal, human, or nucleated cells from other multicellular organisms) may also contain sequences necessary for the termination of transcription and for stabilizing the mRNA. Such sequences are commonly available from the 5' and, occasionally 3', untranslated regions of eukaryotic or viral DNAs or cDNAs.

Construction of suitable vectors containing one or more of the above-listed components employs standard techniques. Isolated plasmids or DNA fragments can be cleaved, tailored, and re-ligated in the form desired to generate the plasmids required. For analysis to confirm correct sequences in plasmids constructed, the ligation mixtures are used to transform host cells, and successful transformants selected by ampicillin or tetracycline resistance where appropriate. Plasmids from the transformants are prepared, analyzed by restriction endonuclease digestion, and/or sequenced.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as Escherichia, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis, Pseudomonas* such as *P. aeruginosa*, and *Streptomyces*. These examples are illustrative rather than limiting.

In addition to prokaryotes, eukaryotic microbes such as filamentous fungi or yeast are suitable expression hosts. Saccharomyces cerevisiae, or common baker's yeast, is the most commonly used among lower eukaryotic host microorganisms. However, a number of other genera, species, and strains are commonly available and useful herein, such as *Schizosaccharomyces pombe; Kluyveromyces* hosts such as *K. lactis, K. fragilis*, etc.; *Pichia pastoris; Candida; Neurospora crassa; Schwanniomyces* such as *Schwanniomyces occidentalis*; and filamentous fungi such as *Penicillium, Tolypocladium*, and *Aspergillus* hosts such as *A. nidulan*, and *A. niger*.

Plant cell cultures of cotton, corn, potato, soybean, petunia, tomato, and tobacco can be utilized as hosts. Typically, plant cells are transfected by incubation with certain strains of the bacterium Agrobacterium tumefaciens. During such incubation of the plant cell culture, the DNA coding sequence is transferred to the plant cell host such that it is transfected, and will, under appropriate conditions, express the DNA. In addition, regulatory and signal sequences compatible with plant cells are available, such as the nopaline synthase promoter and polyadenylation signal sequences.

Host cells are transfected with the above-described expression vectors for RSPO surrogate production, and cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily skilled artisan.

Small Molecule Compositions. RSPO surrogates of the invention can also include organic molecules, preferably small organic compounds having a molecular weight of more than 50 and less than about 20,000 daltons. Useful surrogates are identified by, for example, a screening assay in which molecules are assayed for high affinity binding to RNF43/ZNRF3, and then joined to a cell targeting domain. A molecule can provide for a binding moiety that will be joined to another binding moiety, or joined to a binding domain as described above for polypeptide agents.

Candidate surrogates comprise functional groups necessary for structural interaction with proteins, particularly hydrogen bonding, and typically include at least an amine, carbonyl, hydroxyl or carboxyl group, preferably at least two of the functional chemical groups. The candidate surrogates often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate surrogates are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642, each of which is incorporated herein by reference.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc. that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Preliminary screens can be conducted by screening for compounds capable of binding to a RNF43/ZNRF3 polypeptide. The binding assays usually involve contacting a RNF43/ZNRF3 polypeptide with one or more test compounds and allowing sufficient time for the protein and test compounds to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in Neurotransmitter Receptor Binding (Yamamura, H. I., et al., eds.), pp. 61-89.

Certain screening methods involve screening for a compound that potentiates Wnt signaling activity. Such methods may involve conducting cell-based assays in which test compounds are contacted with one or more cells expressing Fzd and then detecting an increase in expression of Wnt-responsive genes, detecting nuclear localization of β-catenin, and the like.

The level of expression or activity can be compared to a baseline value. As indicated above, the baseline value can be a value for a control sample or a statistical value that is representative of expression levels for a control population. Expression levels can also be determined for cells that do not express a Wnt receptor, as a negative control. Such cells generally are otherwise substantially genetically the same as the test cells. Various controls can be conducted to ensure that an observed activity is authentic including running parallel reactions with cells that lack the reporter construct or by not contacting a cell harboring the reporter construct with test compound. Compounds can also be further validated as described below.

Compounds that are initially identified by any of the foregoing screening methods can be further tested to validate the apparent activity. The basic format of such methods involves administering a lead compound identified during an initial screen to an animal or in a cell culture model that serves as a model for humans. The animal models utilized in validation studies generally are mammals. Specific examples of suitable animals include, but are not limited to, primates, mice, and rats.

Active test agents identified by the screening methods described herein can serve as lead compounds for the synthesis of analog compounds. Typically, the analog compounds are synthesized to have an electronic configuration and a molecular conformation similar to that of the lead compound. Identification of analog compounds can be performed through use of techniques such as self-consistent field (SCF) analysis, configuration interaction (CI) analysis, and normal mode dynamics analysis. Computer programs

RSPO SURROGATES AND WNT SIGNALING

RSPO surrogates, and methods for their use are provided. These and other objects, advantages, and features of the invention will become apparent to those persons skilled in the art upon reading the details of the compositions and methods as more fully described below.

An RSPO surrogate molecule is defined by its physical and biological properties. The sequence of the surrogate is other than a native RSPO protein. An RSPO surrogate as used herein comprises (i) a specific binding domain for RNF43 or ZNRF3 and (ii) a cell targeting domain. The domains may be directly joined, or may be separated by a linker, e.g. a polypeptide linker, or a non-peptidic linker, etc. The length of the linker, and therefore the spacing between the binding domains can be used to modulate the signal strength, and can be selected depending on the desired use of the RSPO surrogate. A polypeptide RSPO surrogate may be a single chain, dimer, or higher order multimer. A key feature of the surrogate is potentiation of Wnt signaling in the canonical β-catenin Wnt signaling cascade, and the β-catenin-independent Plana Cell Polarity (PCP) pathway in a cell. In some embodiments the cell is a mammalian cell, e.g. a human cell.

The term "Wnt potentiating activity" refers to the ability of an RSPO surrogate to potentiate the effect or activity of a Wnt protein binding to a frizzled protein. The ability of the surrogates of the invention to enhance the activity of Wnt can be confirmed by a number of assays. As used herein, the term "enhances" refers to a measurable increase in the level of Wnt/β-catenin signaling or Wnt/PCP signaling compared with the level in the absence of a surrogate of the invention.

In some embodiments the RSPO surrogate circumvents the requirement for expression of the RSPO cognate receptors LGR4, LGR5 or LGR6 for potentiation of Wnt signaling. In other embodiments the RSPO surrogate specifically targets one or more of LGR4, LGR5 or LGR6 for potentiation of Wnt signaling thus providing enhanced selectivity for RSPO activity.

The RNF43 or ZNRF3 binding domain may be selected from any domain that binds RNF43 or ZNRF3 at high affinity, e.g. a Kd of not more than about $1\times10^{-6}$ M, not more about $1\times10^{-7}$ M, not more about $1\times10^{-8}$ M, not more about $1\times10^{-9}$ M or not more about $1\times10^{-10}$ M. Suitable binding domains include, without limitation, de novo designed binding proteins, antibody derived binding proteins, e.g. scFv, Fab, etc. and other portions of antibodies that specifically bind to RNF43 or ZNRF3 proteins; nanobody derived binding domains; knottin-based engineered scaffolds; norrin and engineered binding fragments derived therefrom, naturally occurring binding domains, and the like. In some embodiments the specific binding domain for RNF43 or ZNRF3 is a binding fragment of RSPO, e.g. comprising, consisting or consisting essentially of an RSPO Furin 1 domain. A binding domain may be affinity selected to enhance binding to a desired protein or plurality of proteins.

The cell targeting domain or element may be selected from any domain that selectively binds to a cell surface protein at high affinity, e.g. a $K_D$ of not more about $1\times10^{-7}$ M, not more than about $1\times10^{-8}$ M, not more than about $1\times10^{-9}$ M, not more than about $1\times10^{-10}$ M. Suitable cell targeting domains include, without limitation, de novo designed binding proteins, antibody derived binding proteins, e.g. scFv, Fab, etc. and other portions of antibodies that specifically bind to cell surface protein; nanobody derived binding domains; knottin-based engineered scaffolds; naturally occurring binding proteins or polypeptides, cytokines, growth factors, and the like. In some embodiments the cell targeting domain is a cytokine or growth factor with a cognate receptor on the targeted cell. In some embodiments the cell targeting domain is an antibody or active fragment thereof with specificity for an antigen present on the targeted cell surface. In some such embodiments the antigen is one or more of LGR4, LGR5 or LGR6, e.g. an antibody that selectively binds to a single LGR protein, i.e. one of LGR4, LGR5 or LGR6. An LGR binding moiety may be selective for an LGR protein of interest, e.g. having a specificity for the desired LGR protein of at least 10-fold, 25-fold, 50-fold, 100-fold, 200-fold or more relative to other LGR proteins.

Specific embodiments of RSPO surrogates include, without limitation, exemplary proteins described here, e.g. an antibody-derived binding domain, e.g. an scFv, specific for human RNF43 or human ZNRF3 joined to a cytokine, e.g. IL-2 or IL-4, as set forth in SEQ ID NO:1-4, where SEQ ID NO:1 provides a surrogate specific for ZNRF3 joined to IL-2; SEQ ID NO:2 provides a surrogate specific for ZNRF3 joined to IL-4; SEQ ID NO:3 provides a surrogate specific for RNF43 joined to IL-2, and SEQ ID NO:4 provides a surrogate specific for RNF43 joined to IL-4.

Alternative specific embodiments include, without limitation, an antibody-derived binding domain, e.g. an scFv, specific for human RNF43 or human ZNRF3 joined to a growth factor, e.g. EGF, NGF, etc. Alternative specific embodiments include, without limitation, antibody-derived binding domain, e.g. an scFv, specific for human RNF43 or human ZNRF3 joined to a an antibody or fragment thereof specific for one of human LGR4, LGR5, or LGR6.

In some such embodiments, the antibody-derived binding domain, e.g. an scFv, specific for human RNF43 or human ZNRF3 comprises 1, 2, 3, 4, 5, or 6 CDR sequences from the antibody-derived portion of SEQ ID NO:1-4. One of skill in the art will understand that a number of definitions of the CDRs are commonly in use, including the Kabat definition (see "Zhao et al. A germline knowledge based computational approach for determining antibody complementarity determining regions." Mol Immunol. 2010; 47:694-700), which is based on sequence variability and is the most commonly used. The Chothia definition is based on the location of the structural loop regions (Chothia et al. "Conformations of immunoglobulin hypervariable regions." Nature. 1989; 342: 877-883). Alternative CDR definitions of interest include, without limitation, those disclosed by Honegger, "Yet another numbering scheme for immunoglobulin variable domains: an automatic modeling and analysis tool." J Mol Biol. 2001; 309:657-670; Ofran et al. "Automated identification of complementarity determining regions (CDRs) reveals peculiar characteristics of CDRs and B cell epitopes." J Immunol. 2008; 181:6230-6235; Almagro "Identification of differences in the specificity-determining residues of antibodies that recognize antigens of different size: implications for the rational design of antibody repertoires." J Mol Recognit. 2004; 17:132-143; and Padlanet al. "Identification of specificity-determining residues in antibodies." Faseb J. 1995; 9:133-139., each of which is herein specifically incorporated by reference.

"Wnt protein signaling" or "Wnt signaling" is used herein to refer to the mechanism by which a biologically active Wnt exerts its effects upon a cell to modulate a cell's activity. Wnt proteins modulate cell activity by binding to Wnt receptors, including proteins from the Frizzled (Fz) family of proteins, proteins from the ROR family of proteins, the proteins LRP5, LRP6 from the LRP family of proteins, the protein FRL1/crypto, and the protein Derailed/Ryk. Once activated by Wnt binding, the Wnt receptor(s) will activate one or more intracellular signaling cascades. These include the canonical Wnt signaling pathway; the Wnt/planar cell polarity (Wnt/PCP) pathway; the Wnt-calcium (Wnt/Ca$^{2+}$) pathway (Giles, R H et al. (2003) Biochim Biophys Acta 1653, 1-24; Peifer, M. et al. (1994) Development 120: 369-380; Papkoff, J. et al (1996) Mol. Cell Biol. 16: 2128-2134; Veeman, M. T. et al. (2003) Dev. Cell 5: 367-377); and other Wnt signaling pathways as is well known in the art.

For example, activation of the canonical Wnt signaling pathway results in the inhibition of phosphorylation of the intracellular protein β-catenin, leading to an accumulation of β-catenin in the cytosol and its subsequent translocation to the nucleus where it interacts with transcription factors, e.g. TCF/LEF, to activate target genes. Activation of the Wnt/PCP pathway activates RhoA, c-Jun N-terminal kinase (JNK), and nemo-like kinase (NLK) signaling cascades to control such biological processes as tissue polarity and cell movement. Activation of the Wnt/Ca$^{2+}$ by, for example, binding of Wnt-4, Wnt-5A or Wnt-11, elicits an intracellular release of calcium ions, which activates calcium sensitive enzymes like protein kinase C (PKC), calcium-calmodulin dependent kinase II (CamKII) or calcineurin (CaCN). By assaying for activity of the above signaling pathways, the biological activity of a Wnt composition can be readily determined. A "biologically active RSPO surrogate" is an RSPO surrogate composition that is able to specifically bind to a Fzd receptor and activate Wnt signaling when provided to a cell in vitro or in vivo, that is, when administered to an animal, e.g. a mammal.

In certain embodiments, an RSPO surrogate of the invention increases signaling of a Wnt pathway by at least about 50%, about 75%, about 100%, about 150%, about 200%, about 300%, about 400%, about 5-fold, about 10-fold, and may increase signaling by 50-fold, 100-fold, 500-fold, or more, relative to the level of Wnt signaling in the absence of the surrogate.

Various methods are known in the art for measuring the level of Wnt signaling. These include, but are not limited to assays that measure: Wnt/β-catenin target gene expression; TCF reporter gene expression; beta-catenin stabilization; LRP phosphorylation; Axin translocation from cytoplasm to cell membrane and binding to LRP. The canonical Wnt/β-catenin signaling pathway ultimately leads to changes in gene expression through the transcription factors TCF7, TCF7L1, TCF7L2 and LEF. The transcriptional response to Wnt activation has been characterized in a number of cells and tissues. As such, global transcriptional profiling by methods well known in the art can be used to assess Wnt/β-catenin signaling activation.

Changes in Wnt-responsive gene expression are generally mediated by TCF and LEF transcription factors. A TCF reporter assay assesses changes in the transcription of TCF/LEF controlled genes to determine the level of Wnt/.beta.-catenin signaling. A TCF reporter assay was first described by Korinek, V. et al., 1997. Also known as TOP/FOP this method involves the use of three copies of the optimal TCF motif CCTTTGATC, or three copies of the mutant motif CCTTTGGCC, upstream of a minimal c-Fos promoter driving luciferase expression (pTOPFLASH and pFOPFLASH, respectively) to determine the transactivational activity of endogenous β-catenin/TCF4. A higher ratio of these two reporter activities (TOP/FOP) indicates higher β-catenin/TCF4 activity.

Various other reporter transgenes that respond to Wnt signals exist intact in animals and therefore, effectively reflect endogenous Wnt signaling. These reporters are based on a multimerized TCF binding site, which drives expression of LacZ or GFP, which are readily detectable by methods known in the art. These reporter genes include: TOP-GAL, BAT-GAL, ins-TOPEGFP, ins-TOPGAL, LEF-EGFP, Axin2-LacZ, Axin2-d2EGFP, LGR5tm1(cre/ERT2), TOPdGFP.

The recruitment of dephosphorylated β-catenin to the membrane, stabilization and phosphorylation status of β-catenin and translocation of β-catenin to the nucleus (Klapholz-Brown Z et al., PLoS One. 2(9) e945, 2007) in some cases mediated by complex formation with TCF transcription factors and TNIK are key steps in the Wnt signaling pathway. Stabilization is mediated by Disheveled family proteins that inhibit the "destruction" complex so that degradation of intracellular β-catenin is reduced, and translocation of β-catenin to the nucleus follows thereafter. Therefore, measuring the level and location of β-catenin in a cell is a good reflection of the level of Wnt/β-catenin signaling. A non-limiting example of such an assay is the "BioImage β-Catenin Redistribution Assay" (Thermo Scientific) which provides recombinant U2OS cells that stably express human β-catenin fused to the C-terminus of enhanced green fluorescent protein (EGFP). Imaging and analysis is performed with a fluorescence microscope or HCS platform allowing the levels and distribution of EGFP-β-catenin to be visualized.

Another way, in which the destruction complex is inhibited, is by removal of Axin by recruitment of Axin to the cytoplasmic tail of the Wnt co-receptor LRP. Axin has been shown to bind preferentially to a phosphorylated form of the LRP tail. Visualization of Axin translocation, for example with a GFP-Axin fusion protein, is therefore another method for assessing levels of Wnt/β-catenin signaling.

In certain embodiments, the surrogates of the invention may enhance Wnt signaling by at least 30%, 35%, 40%, 45%, 50%, 60%, 70%, 75%, 80%, 85%, 90%, 95%, 100%, 110%, 150%, 200%, 250%, 300%, 400% or 500% compared to the signaling induced by a neutral substance or negative control as measured in an assay described above, for example as measured in the TOPFlash assay. A negative control may be included in these assays. In particular embodiments, the surrogates of the invention may enhance β-catenin signaling by a factor of 2×, 5×, 10×, 100×, 1000×, 10000× or more as compared to the activity in the absence of the agonist when measured in an assay described above, for example when measured in the TOPFlash assay, or any of the other assays mentioned herein.

Alternatively the activity of the surrogate may be determined by measuring the ubiquitination and/or destruction of frizzled receptors on a targeted cell, where an active RSPO surrogate results in a greater number of frizzled proteins remaining on the cell surface, and unmodified by ubiquitination, e.g. an increase of at least about 5%, at least about 10%, at least about 20%, at least about 50%, or more.

An RSPO surrogate may be fused or bonded to an additional polypeptide sequence. Examples include immunoadhesins, which combine a surrogate with an immunoglobulin sequence particularly an Fc sequence, and epitope tagged polypeptides, which comprise a native inhibitors polypeptide or portion thereof fused to a "tag polypeptide". The tag polypeptide has enough residues to provide an epitope against which an antibody can be made, yet is short enough such that it does not interfere with biological activity of the native inhibitors polypeptide. Suitable tag polypeptides generally have at least six amino acid residues and usually between about 6-60 amino acid residues.

Pharmaceutical Compositions

For therapeutic applications, the RSPO surrogate is administered to a mammal, including a human, in a physiologically acceptable dosage form, including those that may be administered to a human intravenously as a bolus or by continuous infusion over a period of time. Alternative routes of administration include topical, intramuscular, intraperitoneal, intra-cerobrospinal, subcutaneous, intra-articular, intrasynovial, intrathecal, oral, topical, or inhalation routes. The RSPO surrogates also are suitably administered by intratumoral, peritumoral, intralesional, or perilesional routes or to the lymph, to exert local as well as systemic therapeutic effects.

Pharmaceutical compositions may also comprise combinations of the molecules of the invention with cells, including stem cells, progenitor cells, and the like. In some embodiments, the compositions comprise the molecules of the invention in combination with regenerative somatic stem cells, e.g. epithelial stem cells, neural stem cells, liver stem cells, hematopoietic stem cells, osteoblasts, muscle stem cells, mesenchymal stem cells, pancreatic stem cells, etc. In such combinations, cells can be pre-treated with a molecule of the invention prior to use, e.g. ex vivo treatment of cells with the RSPO surrogate; cells can be administered concomitantly with a molecule of the invention in a separate or combined formulation; cells can be provided to an individual prior to treatment with a molecule of the invention, and the like.

The terms "stem cell" as used herein, refer to a cell that has the property of self-renewal and has the developmental potential to differentiate into multiple cell types. A stem cell is capable of proliferation and giving rise to more such stem cells while maintaining its developmental potential. Stem cells can divide asymmetrically, with one daughter cell retaining the developmental potential of the parent stem cell and the other daughter cell expressing some distinct other specific function, phenotype and/or developmental potential from the parent cell. The daughter cells themselves can be induced to proliferate and produce progeny that subsequently differentiate into one or more mature cell types, while also retaining one or more cells with parental developmental potential. A differentiated cell may derive from a multipotent cell, which itself is derived from a multipotent cell, and so on. While each of these multipotent cells may be considered stem cells, the range of cell types each such stem cell can give rise to, i.e., their developmental potential, can vary considerably. Alternatively, some of the stem cells in a population can divide symmetrically into two stem cells, known as stochastic differentiation, thus maintaining some stem cells in the population as a whole, while other cells in the population give rise to differentiated progeny only. Accordingly, the term "stem cell" refers to any subset of cells that have the developmental potential, under particular circumstances, to differentiate to a more specialized or differentiated phenotype, and which retain the capacity, under certain circumstances, to proliferate without substantially differentiating.

The term "somatic stem cell" is used herein to refer to any pluripotent or multipotent stem cell derived from non-embryonic tissue, including fetal, juvenile, and adult tissue. Natural somatic stem cells have been isolated from a wide variety of adult tissues including blood, bone marrow, brain, olfactory epithelium, skin, pancreas, skeletal muscle, and cardiac muscle. The term "progenitor cell" is used herein to refer to cells that are at an earlier stage along a developmental pathway or progression, relative to a cell which it can give rise to by differentiation. Often, progenitor cells have significant or very high proliferative potential. Progenitor cells can give rise to multiple distinct differentiated cell types, or to a single differentiated cell type, depending on the developmental pathway and on the environment in which the cells develop and differentiate.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$ Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The effective amount of a therapeutic composition to be given to a particular patient will depend on a variety of factors, several of which will be different from patient to patient. A formulation may be provided, for example, in a unit dose. A competent clinician will be able to determine an effective amount of a therapeutic agent to administer to a patient. Dosage of the surrogate will depend on the treatment, route of administration, the nature of the therapeutics, sensitivity of the disease to the therapeutics, etc. Utilizing $LD_{50}$ animal data, and other information available, a clinician can determine the maximum safe dose for an individual, depending on the route of administration. Compositions which are rapidly cleared from the body may be administered at higher doses, or in repeated doses, in order to maintain a therapeutic concentration. Utilizing ordinary skill, the competent clinician will be able to optimize the dosage of a particular therapeutic or imaging composition in the course of routine clinical trials. Typically the dosage will be 0.001 to 100 milligrams of agent per kilogram subject body weight.

The compositions can be administered to the subject in a series of more than one administration. For therapeutic compositions, regular periodic administration (e.g., every 2-3 days) will sometimes be required, or may be desirable to reduce toxicity. For therapeutic compositions which will be utilized in repeated-dose regimens, moieties which do not provoke immune responses are preferred.

In another embodiment of the invention, an article of manufacture containing materials useful for the treatment of the conditions described herein is provided. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). The active agent in the composition is the RSPO surrogate. The label on, or associated with, the container indicates that the composition is used for treating the condition of choice. Further container(s) may be provided with the article of manufacture which may hold, for example, a pharmaceutically-acceptable buffer, such as phosphate-buffered saline, Ringer's solution or dextrose solution. The article of manufacture may further include other materials desirable from a commercial and user standpoint, including other buffers, diluents, filters, needles, syringes, and package inserts with instructions for use.

As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, stabilizes one or more characteristics of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment.

For example, in some embodiments, term "therapeutically effective amount", refers to an amount which, when administered to an individual in need thereof in the context of inventive therapy, will block, stabilize, attenuate, or reverse a disease process occurring in said individual.

Methods of Use

The RSPO surrogates are useful for both prophylactic and therapeutic purposes. Thus, as used herein, the term "treating" is used to refer to both prevention of disease, and treatment of a pre-existing condition. In certain instances, prevention indicates inhibiting or delaying the onset of a disease or condition, in a patient identified as being at risk of developing the disease or condition. The treatment of ongoing disease, to stabilize or improve the clinical symptoms of the patient, is a particularly important benefit provided by the present invention. Such treatment is desirably performed prior to loss of function in the affected tissues; consequently, the prophylactic therapeutic benefits provided by the invention are also important. Evidence of therapeutic effect may be any diminution in the severity of disease. The therapeutic effect can be measured in terms of clinical outcome or can be determined by immunological or biochemical tests. Patients for treatment may be mammals, e.g. primates, including humans, may be laboratory animals, e.g. rabbits, rats, mice, etc., particularly for evaluation of therapies, horses, dogs, cats, farm animals, etc.

The dosage of the therapeutic formulation, e.g., pharmaceutical composition, will vary widely, depending upon the nature of the condition, the frequency of administration, the manner of administration, the clearance of the agent from the host, and the like. In particular embodiments, the initial dose can be larger, followed by smaller maintenance doses. In certain embodiments, the dose can be administered as infrequently as weekly or biweekly, or more often fractionated into smaller doses and administered daily, semi-weekly, or otherwise as needed to maintain an effective dosage level.

In some embodiments of the invention, administration of the composition or formulation comprising the RSPO surrogate is performed by local administration. Local administration, as used herein, may refer to topical administration, but also refers to injection or other introduction into the body at a site of treatment. Examples of such administration include intramuscular injection, subcutaneous injection, intraperitoneal injection, and the like. In other embodiments, the composition or formulation comprising the RSPO surrogate is administered systemically, e.g., orally or intravenously. In one embodiment, the composition of formulation comprising the RSPO surrogate is administered by infusion, e.g., continuous infusion over a period of time, e.g., 10 min, 20 min, 3 min, one hour, two hours, three hours, four hours, or greater.

In some embodiments of the invention, the compositions or formulations are administered on a short term basis, for example a single administration, or a series of administrations performed over, e.g. 1, 2, 3 or more days, up to 1 or 2 weeks, in order to obtain a rapid, significant increase in activity. The size of the dose administered must be determined by a physician and will depend on a number of factors, such as the nature and gravity of the disease, the age and state of health of the patient and the patient's tolerance to the drug itself.

In certain methods of the present invention, an effective amount of a composition comprising a RSPO surrogate is provided to cells, e.g. by contacting the cell with an effective amount of that composition to achieve a desired effect, e.g. to potentiate Wnt signaling, proliferation, etc. In particular embodiments, the contacting occurs in vitro, ex vivo or in vivo. In particular embodiments, the cells are derived from or present within a subject in need or increased Wnt signaling.

In some methods of the invention, an effective amount of the subject composition is provided to potentiate Wnt signaling in a cell. Biochemically speaking, an effective amount or effective dose of a RSPO surrogate is an amount to increase Wnt signaling in a cell by at least 30%, at least 40%, at least 50%, at least 60%, at least 70%, at least 80%, at least 90%, at least 95%, or by 100% relative to the signaling in the absence of the surrogate. The amount of modulation of a cell's activity can be determined by a number of ways known to one of ordinary skill in the art of Wnt biology.

In a clinical sense, an effective dose of a RSPO surrogate composition is the dose that, when administered to a subject for a suitable period of time, e.g., at least about one week, and maybe about two weeks, or more, up to a period of about 4 weeks, 8 weeks, or longer, will evidence an alteration in the symptoms associated with lack of Wnt signaling. In some embodiments, an effective dose may not only slow or halt the progression of the disease condition but may also induce the reversal of the condition. It will be understood by those of skill in the art that an initial dose may be administered for such periods of time, followed by maintenance doses, which, in some cases, will be at a reduced dosage.

The calculation of the effective amount or effective dose of RSPO surrogate composition to be administered is within the skill of one of ordinary skill in the art, and will be routine to those persons skilled in the art. Needless to say, the final amount to be administered will be dependent upon the route of administration and upon the nature of the disorder or condition that is to be treated.

Cells suitable for use in the subject methods are generally cells that comprise one or more Fzd receptors, where the ubiquitination of the Fzd receptor is decreased by administration of the RSPO surrogate. The cells to be contacted may be in vitro, that is, in culture, or they may be in vivo, that is, in a subject. Cells may be from/in any organism, but are preferably from a mammal, including humans, domestic and farm animals, and zoo, laboratory or pet animals, such as dogs, cats, cattle, horses, sheep, pigs, goats, rabbits, rats, mice, frogs, zebrafish, fruit fly, worm, etc. Preferably, the mammal is human. Cells may be from any tissue. Cells may be frozen, or they may be fresh. They may be primary cells, or they may be cell lines. Often cells are primary cells used in vivo, or treated ex vivo prior to introduction into a recipient.

Cells in vitro may be contacted with a composition comprising a RSPO surrogate by any of a number of well-known methods in the art. For example, the protein composition may be provided to the cells in the media in which the subject cells are being cultured. Nucleic acids encoding the RSPO surrogate may be provided to the subject cells or to cells co-cultured with the subject cells on vectors under conditions that are well known in the art for promoting their uptake, for example electroporation, calcium chloride transfection, and lipofection. Alternatively, nucleic acids encoding the RSPO surrogate may be provided to the subject cells or to cells cocultured with the subject cells via a virus, i.e. the cells are contacted with viral particles comprising nucleic acids encoding the Wnt peptide surrogate polypeptide. Retroviruses, for example, lentiviruses, are particularly suitable to the method of the invention, as they can be used to transfect non-dividing cells (see, for example, Uchida et al. (1998) P.N.A.S. 95(20):11939-44). Commonly used retroviral vectors are "defective", i.e. unable to produce viral proteins required for productive infection. Rather, replication of the vector requires growth in a packaging cell line.

Likewise, cells in vivo may be contacted with the subject RSPO surrogate compositions by any of a number of well-known methods in the art for the administration of proteins, peptides, small molecules, or nucleic acids to a subject. The RSPO surrogate composition can be incorporated into a variety of formulations or pharmaceutical compositions, which in some embodiments will be formulated in the absence of detergents, liposomes, etc., as have been described for the formulation of full-length Wnt proteins.

WNT signaling is required for the healing of almost every tissue in the human body. For example, WNTs have been shown to activate adult, tissue-resident stem cells. These stem cells self-renew and divide, and in doing so give rise to progeny cells that mature into the tissue of interest. The molecules of the present invention potentiate WNT activity in a pharmacologically acceptable format.

In some embodiments, the compounds of the invention are administered for use in treating diseased or damaged tissue, for use in tissue regeneration and for use in cell growth and proliferation, and/or for use in tissue engineering. In particular, the present invention provides an RSPO surrogate, or a composition comprising one or more surrogates according to the invention for use in treating tissue loss or damage due to aging, trauma, infection, or other pathological conditions.

Conditions of interest for treatment with the compositions of the invention include, without limitation, a number of conditions in which regenerative cell growth is desired. Such conditions can include, for example, enhanced bone growth or regeneration, e.g. on bone regeneration, bone grafts, healing of bone fractures, etc.; treatment of alopecia; enhanced regeneration of sensory organs, e.g. treatment of hearing loss, treatment of macular degeneration, etc.; tooth growth, tooth regeneration, treatment of stroke, traumatic brain injury, Alzheimer's disease, multiple sclerosis and other conditions affecting the blood brain barrier; treatment of oral mucositis, conditions where enhanced epidermal regeneration is desired, e.g. epidermal wound healing, treatment of diabetic foot ulcers, etc., enhanced growth of hematopoietic cells, e.g. enhancement of hematopoietic stem cell transplants from bone marrow, mobilized peripheral blood, treatment of immunodeficiencies, etc.; enhanced regeneration of liver cells, e.g. liver regeneration, treatment of cirrhosis, enhancement of liver transplantations, and the like.

Conditions in which enhanced bone growth is desired may include, without limitation, fractures, grafts, ingrowth around prosthetic devices, and the like. WNT proteins are critical regulators of bone turnover, and abundant scientific data supports a role for these proteins in promoting bone regeneration. In some embodiments, bone marrow cells are exposed to molecules of the invention, such that stem cells within that marrow become activated. These activated cells can remain in situ for the benefit of the individual, or can be used in bone grafting procedures.

In some embodiments, bone regeneration is enhanced by contacting a responsive cell population, e.g. bone marrow, bone progenitor cells, bone stem cells, etc. with an effective dose of a molecule of the invention. In some such embodiments, the contacting is performed in vivo. In other such embodiments, the contacting is performed ex vivo. The molecule may be localized to the site of action, e.g. by loading onto a matrix, which is optionally biodegradable, and optionally provides for a sustained release of the active agent. Matrix carriers include, without limitation, absorbable collagen sponges, ceramics, hydrogels, bone cements, and the like.

Compositions comprising one or more of the molecules of the invention can be used in the in vitro generation of skeletal tissue, such as from skeletogenic stem cells, as well as the in vivo treatment of skeletal tissue deficiencies. The subject compounds may be used to regulate the rate of chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions. For example, the compositions of the present invention can be used as part of a regimen for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a laxation of a joint by a torn ligament, malignment of joints, bone fracture, or by hereditary disease.

The compositions of the invention also find use in regeneration of tissues in the eye. Age-related macular degeneration (AMD) is characterized by progressively decreased central vision and visual acuity and remains a leading cause of vision loss and blindness in aged Americans. Currently, the standard of care for AMD is intravitreal vascular endothelial growth factor (VEGF) inhibitors. AMD is a multi-factorial disease involving numerous pathogenic factors, such as VEGF, platelet-derived growth factor (PDGF), intercellular adhesion molecule-1 (ICAM-1), tumor necrosis factor-alpha (TNF-α), cyclooxygenase-2 (Cox-2), connective tissue growth factor (CTGF), and fibronectin (FN), that contribute to angiogenesis, inflammation, fibrosis and oxidative stress in AMD. Compositions of the present invention can be used, for example, in an infusion; in a matrix or other depot system; or other topical application to the eye for treatment of macular degeneration.

In other embodiments, the compositions of the invention are used in the regeneration of retinal tissue. In the adult mammalian retina, Müller glia dedifferentiate and produce retinal cells, including photoreceptors, for example after neurotoxic injury in vivo. However, the number of newly generated retinal neurons is very limited. However Wnt signaling can promote proliferation of Müller glia-derived retinal progenitors and neural regeneration after damage or during degeneration. Compositions of the present invention can be used, for example, in an infusion; in a matrix or other depot system; or other topical application to the eye for enhancement of retinal regeneration.

Other sensory organs, such as the cells involved in hearing loss, also benefit from the compositions of the invention. In the inner ear, the auditory organ houses mechanosensitive hair cells required for translating sound vibration to electric impulses. The vestibular organs, comprised of the semicircular canals (SSCs), the utricle, and the saccule, also contain sensory hair cells in order to detect head position and motion. Both auditory and vestibular signals are in turn relayed centrally via the spiral and vestibular ganglion neurons, allowing for sound and balance perception. Numerous studies have characterized the multiple roles of the Wnt signaling pathway during cochlear development and in promoting hair cell regeneration. Mature mammalian auditory and vestibular organs do not spontaneously mount a proliferative response after hair cell degeneration. However, active Wnt/β-catenin signaling can promote proliferation of hair cells, where LGR5-positive supporting cells can behave as hair cell progenitors. LGR5-positive supporting cells can mitotically regenerate hair cells, where Wnt signaling augments both the mitotic response and the extent of hair cell regeneration. Wnt signaling can also induce ectopic hair cell formation. Compositions of the present invention can be used, for example, in an infusion; in a matrix or other depot system; or other topical application to the ear for enhancement of auditory regeneration.

Periodontal diseases are a leading cause of tooth loss and are linked to multiple systemic conditions. Reconstruction of the support and function of affected tooth-supporting tissues represents an important therapeutic endpoint for periodontal regenerative medicine. An improved understanding of periodontal biology coupled with current advances in scaffolding matrices provides treatments that provide the compositions of the invention, optionally in combination with delivery of regenerative cells for the predictable tissue regeneration of supporting alveolar bone, periodontal ligament, and cementum. In some embodiments, tooth or underlying bone regeneration is enhanced by contacting a responsive cell population with an effective dose of a molecule of the invention. In some such embodiments, the contacting is performed in vivo. In other such embodiments, the contacting is performed ex vivo, with subsequent implantation of the activated stem or progenitor cells. The molecule may be localized to the site of action, e.g. by loading onto a matrix, which is optionally biodegradable, and optionally provides for a sustained release of the active agent. Matrix carriers include, without limitation, absorbable collagen sponges, ceramics, hydrogels, bone cements, and the like.

Hair loss is a common problem with multiple causes that range from hormone sensitivity to autoimmunity. Androgenetic alopecia, often called male pattern baldness, is the most common form of hair loss in men, which affects as many as 50% of men as they age. In androgenetic alopecia, hair loss is caused by a sensitivity of hair follicles in the top of the scalp to the androgen 5α-dihydrotestosterone (DHT). DHT causes those follicles to undergo a progressive miniaturization to the point where they no longer produce a clinically apparent hair shaft. The cells affected by DHT are the dermal papilla cells, which cease growing and lose their ability to direct hair growth. Epidermal Wnt signaling is critical for adult hair follicle regeneration. In some embodiments, hair follicle regeneration is enhanced by contacting a responsive cell population with an effective dose of a molecule of the invention. In some such embodiments, the contacting is performed in vivo. In other such embodiments, the contacting is performed ex vivo, with subsequent implantation of the activated stem or progenitor cells, e.g. follicular cells. The molecule may be localized to the site of action, e.g. topical lotions, gels, creams and the like.

Various epidermal conditions benefit from treatment with the compounds of the invention. Mucositis occurs when there is a break down of the rapidly divided epithelial cells lining the gastro-intestinal tract, leaving the mucosal tissue open to ulceration and infection. Mucosal tissue, also known as mucosa or the mucous membrane, lines all body passages that communicate with the air, such as the respiratory and alimentary tracts, and have cells and associated glands that secrete mucus. The part of this lining that covers the mouth, called the oral mucosa, is one of the most sensitive parts of the body and is particularly vulnerable to chemotherapy and radiation. The oral cavity is the most common location for mucositis. Oral mucositis is probably the most common, debilitating complication of cancer treatments, particularly chemotherapy and radiation. It can lead to several problems, including pain, nutritional problems as a result of inability to eat, and increased risk of infection due to open sores in the mucosa. It has a significant effect on the patient's quality of life and can be dose-limiting (i.e., requiring a reduction in subsequent chemotherapy doses). Other epidermal conditions include epidermal wound healing, diabetic foot ulcers, and the like. Molecules of the invention can find use in such conditions, where regenerative cells are contacted with compounds of the invention. Contacting can be, for example, topical, including intradermal, subdermal, in a gel, lotion, cream etc. applied at targeted site, etc.

The liver has a capacity for regeneration, which can be enhanced by Wnt signaling. Adult hepatic progenitor (oval) cells are facultative stem cells in liver. Active Wnt/β-catenin signaling occurs preferentially within the oval cell population, and Wnt signaling promotes expansion of the oval cell population in a regenerated liver. Methods for regeneration of liver tissue benefits from administration of the compounds of the invention, which can be systemic or localized, e.g. by injection into the liver tissue, by injection into veins leading into the liver, by implantation of a sustained release formulation, and the like. Liver damage can be associated with infection, alcohol abuse, etc.

Stroke, traumatic brain injury, Alzheimer's, multiple sclerosis and other conditions affecting the blood-brain barrier. Angiogenesis is critical to ensure the supply of oxygen and nutrients to many tissues throughout the body, and is especially important for the CNS as the neural tissue is extremely sensitive to hypoxia and ischemia. The blood vessels in the brain form a specialized structure, termed the blood brain barrier (BBB), which limits the flow of molecules and ions from the blood to the brain. This BBB is critical to maintain brain homeostasis and protect the CNS from toxins and pathogens. CNS endothelial cells which form the BBB differ from endothelial cells in non-neural tissue, in that they are highly polarized cells held together by tight junctions that limit the paracellular flow of molecules and ions. In addition, CNS endothelial cells also express specific transporters, both to provide selective transport of essential nutrients across the BBB into the brain and to efflux potential toxins from the brain. Wnt signaling specifically regulates CNS vessel formation and/or function. Conditions in which the BBB is compromised can benefit from administration of the compounds of the invention, e.g. by direct injection, intrathecal administration, implantation of sustained release formulations, and the like.

The patient may be any animal (e.g., a mammal), including, but not limited to, humans, non-human primates, rodents, and the like. Typically, the patient is human. The methods of treatment and medical uses of the surrogates of the invention or compounds or compositions comprising surrogates of the invention promote tissue regeneration. The term "tissue" refers to part of an organism consisting of a cell or an aggregate of cells, optionally having a similar structure, function and/or origin. Examples of tissues include but are not limited to: epithelial tissues, such as skin tissue, stomach lining, pancreatic lining, liver; connective tissues, such as inner layers of skin, tendons, ligaments, cartilage, bone, fat, hair, blood; muscle tissues; and nerve tissues, such as glial cells and neurons. The loss or damage can be anything which causes the cell number to diminish. For example, an accident, an autoimmune disorder, a therapeutic side-effect or a disease state could constitute trauma. Specific examples of conditions which may cause cell number to diminish include, but are not limited to: radiation/chemotherapy, mucositis, IBD, short bowel syndrome, hereditary bowel disorders, celiac disease, metabolic diseases, hereditary syndromes, (viral) infections (HepB/C), toxic states, alcoholic liver, fatty liver, cirrhosis, infections, pernicious anemia, ulceration, diabetes, diabetic foot ulcers (e.g., refractory diabetic foot ulcers), destruction of islet cells, loss of bone mass (osteoporosis), loss of functional skin, loss of hair, loss of functional lung tissue, loss of kidney tissue (for instance acute tubulus necrosis), loss of sensory cells in the inner ear. Tissue regeneration increases the cell number within the tissue and preferably enables connections between cells of the tissue to be re-established, and more preferably the functionality of the tissue to be regained.

Other conditions that may be treated with the surrogates or compositions comprising one or more surrogates of the invention include but are not limited to: joint disorders, osteoporosis and related bone diseases, baldness, graft-versus-host disease.

Surrogates or compositions comprising one or more surrogates of the invention may also be used for wound healing and generation of smooth muscle tissues in many organs (e.g. airways, large arteries, uterus).

In some embodiments, the invention provides methods of treatment and medical uses, as described previously, wherein two or more surrogates of the invention or compounds or compositions comprising surrogates of the invention, are administered to an animal or patient simultaneously, sequentially, or separately. The surrogate(s) may also be administered simultaneously, sequentially, or separately with a Wnt protein or surrogate thereof.

In some embodiments, the invention provides methods of treatment and medical uses, as described previously, wherein one or more surrogates of the invention or compounds or compositions comprising surrogates of the invention, is administered to an animal or patient in combination with one or more further compound or drug, and wherein said surrogates of the invention or compounds or compositions comprising surrogates of the invention and said further compound or drug are administered simultaneously, sequentially, or separately.

The surrogates of the invention also have widespread applications in non-therapeutic methods, for example in vitro research methods.

The invention provides a method for tissue regeneration of damaged tissue, such as the tissues discussed in the section of medical uses above, comprising administering a surrogate of the invention. The surrogate may be administered directly to the cells in vivo, administered to the patient orally, intravenously, or by other methods known in the art, or administered to ex vivo cells. In some embodiments where the surrogate of the invention is administered to ex vivo cells, these cells may be transplanted into a patient before, after or during administration of the agonist of the invention.

The invention also provides a method for enhancing the proliferation of cells comprising supplying the cells with a surrogate of the invention. These methods may be carried out in vivo, ex vivo or in vitro.

Wnt signaling is a key component of stem cell culture. For example, the stem cell culture media as described in WO2010/090513, WO2012/014076, Sato et al., 2011 (GASTROENTEROLOGY 2011; 141:1762-1772) and Sato et al., 2009 (Nature 459, 262-5). The surrogates of the invention are suitable alternatives to RSPO for use in these stem cell culture media, or may be combined with RSPO.

Accordingly, in one embodiment, the invention provides a method for enhancing the proliferation of stem cells comprising supplying stem cells with surrogates of the invention in combination with a Wnt protein or surrogate thereof. In one embodiment, the invention provides a cell culture medium comprising one or more proteins of the invention. In some embodiments, the cell culture medium may be any cell culture medium already known in the art that normally comprises Wnt or RSPO, but wherein the Wnt or RSPO is replaced (wholly or partially) or supplemented by surrogates of the invention. For example, the culture medium may be as described in WO2010/090513, WO2012/014076, Sato et al., 2011 (GASTROENTEROLOGY 2011; 141:1762-1772) and Sato et al., 2009 (Nature 459, 262-5), which are hereby incorporated by reference in their entirety.

Stem cell culture media often comprise additional growth factors. This method may thus additionally comprise supplying the stem cells with a growth factor. Growth factors commonly used in cell culture medium include epidermal growth factor (EGF, (Peprotech), Transforming Growth Factor-alpha (TGF-alpha, Peprotech), basic Fibroblast Growth Factor (bFGF, Peprotech), brain-derived neurotrophic factor (BDNF, R&D Systems), Human Growth Factor (HGF) and Keratinocyte Growth Factor (KGF, Peprotech, also known as FGF7). EGF is a potent mitogenic factor for a variety of cultured ectodermal and mesodermal cells and has a profound effect on the differentiation of specific cells in vivo and in vitro and of some fibroblasts in cell culture. The EGF precursor exists as a membrane-bound molecule which is proteolytically cleaved to generate the 53-amino acid peptide hormone that stimulates cells. EGF or other mitogenic growth factors may thus be supplied to the stem cells. During culturing of stem cells, the mitogenic growth factor may be added to the culture medium every second day, while the culture medium is refreshed preferably every fourth day. In general, a mitogenic factor is selected from the groups consisting of: i) EGF, TGF-.alpha. and KGF, ii) EGF, TGF-.alpha. and FGF7; iii) EGF, TGF-.alpha. and FGF; iv) EGF and KGF; v) EGF and FGF7; vi) EGF and a FGF; vii) TGF-α and KGF; viii) TGF-.alpha. and FGF7; ix) or from TGF α and a FGF.

These methods of enhancing proliferation of stem cells can be used to grow new organoids and tissues from stem cells, as for example described in WO2010/090513 WO2012/014076, Sato et al., 2011 (GASTROENTEROLOGY 2011; 141:1762-1772) and Sato et al., 2009 (Nature 459, 262-5).

A number of clinically relevant conditions are characterized by an inability to regenerate tissues, where potentiation of Wnt signaling is desirable.

In some embodiments the RSPO surrogate is used to enhance stem cell regeneration. Stem cells of interest include muscle satellite cells; hematopoietic stem cells and progenitor cells derived therefrom (U.S. Pat. No. 5,061, 620); neural stem cells (see Morrison et al. (1999) Cell 96: 737-749); embryonic stem cells; mesenchymal stem cells; mesodermal stem cells; liver stem cells, etc.

The RSPO surrogates find use in enhancing bone healing. In many clinical situations, the bone healing condition are less ideal due to decreased activity of bone forming cells, e.g. within aged people, following injury, in osteogenesis imperfecta, etc. A variety of bone and cartilage disorders affect aged individuals. Such tissues are normally regenerated by mesenchymal stem cells. Included in such conditions is osteoarthritis. Osteoarthritis occurs in the joints of the body as an expression of "wear-and-tear". Thus athletes or overweight individuals develop osteoarthritis in large joints (knees, shoulders, hips) due to loss or damage of cartilage. This hard, smooth cushion that covers the bony joint surfaces is composed primarily of collagen, the structural protein in the body, which forms a mesh to give support and flexibility to the joint. When cartilage is damaged and lost, the bone surfaces undergo abnormal changes. There is some inflammation, but not as much as is seen with other types of arthritis. Nevertheless, osteoarthritis is responsible for considerable pain and disability in older persons.

In methods of accelerating bone repair, a pharmaceutical composition of the present invention is administered to a patient suffering from damage to a bone, e.g. following an injury. The formulation is preferably administered at or near the site of injury, following damage requiring bone regeneration. The Wnt formulation is preferably administered for a short period of time, and in a dose that is effective to increase the number of bone progenitor cells present at the site of injury. In some embodiments the Wnt is administered within about two days, usually within about 1 day of injury, and is provided for not more than about two weeks, not more than about one week, not more than about 5 days, not more than about 3 days, etc.

In an alternative method, patient suffering from damage to a bone is provided with a composition comprising bone marrow cells, e.g. a composition including mesenchymal stem cells, bone marrow cells capable of differentiating into osteoblasts; etc. The bone marrow cells may be treated ex vivo with a pharmaceutical composition comprising a Wnt protein or proteins in a dose sufficient to enhance regeneration; or the cell composition may be administered to a patient in conjunction with a Wnt formulation of the invention.

Sequences

An scFv antibody fragments recognizing ZNRF3 is fused to human IL-2 in an exemplary construct as follows:

```
Z6 scFv-human IL2 (SEQ ID NO: 1):
ASQVQLVQSGAEVKNPGASVKVSCKASGYAFTSYGISWVRQAPGQGLEWM

GWISAYTRNTNYAQKFQGRVTLTTDTSTSTAYMELRSLRSDDTAIYYCAR

DARYSLGVGAFDVWGQGTMVTVSSGILGSGGGSGGGGSGGGGSETTLTQ

SPAFMSATPGDKVSISCKASRDIDDDLNWYQQKPGEAAISIIQEATTLVP

GIPPRFSGSGYGTDFTLTINNIESEDAAYYFCLQHDDVPYTFGQGTKLEI

KSGILGSGSGSGSAPTSSSTKKTQLQLEHLLLDLQMILNGINNYKNPK

LTRMLTFKFYMPKKATELKHLQCLEEELKPLEEVLNLAQSKNFHLRPRDL

ISNINVIVLELKGSETTFMCEYADETATIVEFLNRWITFCQSIISTLTAA

AHHHHHHH.
```

The components of the sequence are as follows:
SEQ ID NO:1, residues 1-255 scFv sequence specific for human ZNRF3. Exemplary CDR sequences are underlined. SEQ ID NO:1 residues 256-265 is a linker. SEQ ID NO:1, residues 266-398 is a human IL-2 sequence. SEQ ID NO:1, residues 399-408 is a histidine tag.

```
ASQVQLVQSGAEVKNPGASVKVSCKASGYAFTSYGISWVRQAPGQGLEWM

GWISAYTRNTNYAQKFQGRVTLTTDTSTSTAYMELRSLRSDDTAIYYCAR

DARYSLGVGAFDVWGQGTMVTVSSGILGSGGGSGGGGSGGGGSETTLTQ

SPAFMSATPGDKVSISCKASRDIDDDLNWYQQKPGEAAISIIQEATTLVP

GIPPRFSGSGYGTDFTLTINNIESEDAAYYFCLQHDDVPYTFGQGTKLEI

KSGIL

GSGSGSGSGS

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT

AAAHHHHHHH
```

The exemplary CDR sequences of the antibody are therefore:

| CRD | Sequence | SEQ ID NO |
|---|---|---|
| VH CDR1 | YAFTSYGIS | 6 |
| VH CDR2 | WISAYTRNTNYAQKFQG | 7 |
| VH CDR3 | DARYSLGVGAFDV | 8 |
| VL CDR1 | KASRDIDDDLN | 9 |
| VL CDR2 | EATTLVP | 10 |
| VL CDR3 | LQHDDVPYT | 11 |

A similar construct with Z6 antibody was made with an IL-4 fusion, as follows: Z6-IL4 (SEQ ID NO:2), where residues 266-394 is the human IL-4 protein.

```
ASQVQLVQSGAEVKNPGASVKVSCKASGYAFTSYGISWVRQAPGQGLEWM

GWISAYTRNTNYAQKFQGRVTLTTDTSTSTAYMELRSLRSDDTAIYYCAR

DARYSLGVGAFDVWGQGTMVTVSSGILGSGGGSGGGGSGGGGSETTLTQ

SPAFMSATPGDKVSISCKASRDIDDDLNWYQQKPGEAAISIIQEATTLVP

GIPPRFSGSGYGTDFTLTINNIESEDAAYYFCLQHDDVPYTFGQGTKLEI

KSGILGSGSGSGSGSHKCDITLQEIIKTLNSLTEQKTLCTELTVTDIFAA

SKNTTEKETFCRAATVLRQFYSHHEKDTRCLGATAQQFHRHKQLIRFLKR

LDRNLWGLAGLNSCPVKEANQSTLENFLERLKTIMREKYSKCSSAAAHHH

HHHHH
```

An scFv antibody fragments recognizing RNF43 is fused to human IL-2 in an exemplary construct as follows:

```
R5 scFv-human IL2 (SEQ ID NO: 3):
ASQITLKESGPTLVKPTQTLTLTCSFSGFSLSFSGVGVAWIRQPPGKALE

WLALIYWDDDKRYSPSLKSRLTITKDTSKNQWLTMTNMDPLDTATYYCAH

REWKAFGAFDIWGQGTMVTVSSGILGSGGGGSGGGGSGGGGSQPVLTQSP

SASGTPGQRVTISCSGSSSNIGSNTVNWYQQLPGTAPKLLIYSNNQRPSG

VPDRFSGSKSVTSASLAISGLQSEDEAEYYCATWDDSLNGAVFGGGTQLT

VLSGILGSGSGSGSGSAPTSSSTKKTQLQLEHLLLDLQMILNGINNYKNP

KLTRMLTFKFYMPKKATELKHLQCLEEELKPLEEVLNLAQSKNFHLRPRD

LISNINVIVLELKGSETTFMCEYADETATIVEFLNRWITFCQSIISTLTA

AAHHHHHHHH
```

The components of the sequence are as follows:
SEQ ID NO:1, residues 1-258 scFv sequence specific for human RNF43. Exemplary CDR sequences are underlined. SEQ ID NO:1 residues 258-268 is a linker. SEQ ID NO:1, residues 268-403 is a human IL-2 sequence. SEQ ID NO:1, residues 404-414 is a histidine tag.

```
ASQITLKESGPTLVKPTQTLTLTCSFSGFSLSFSGVGVAWIRQPPGKALE

WLALIYWDDDKRYSPSLKSRLTITKDTSKNQVVLTMTNMDPLDTATYYCA

HREWKAFGAFDIWGQGTMVTVSSGILGSGGGGSGGGGSGGGGSQPVLTQS
```

-continued

PSASGTPGQRVTISCSGSSSNIGSNTVNWYQQLPGTAPKWYSNNQRPSGV

PDRFSGSKSVTSASLAISGLQSEDEAEYYCATWDDSLNGAVFGGGTQLTV

LSGIL

GSGSGSGSGS

APTSSSTKKTQLQLEHLLLDLQMILNGINNYKNPKLTRMLTFKFYMPKKA

TELKHLQCLEEELKPLEEVLNLAQSKNFHLRPRDLISNINIVIVLELKGSE

TTFMCEYADETATIVEFLNRWITFCQSIISTLT

AAAHHHHHHHH

The exemplary CDR sequences of the antibody are therefore:

| CRD | Sequence | SEQ ID NO |
|---|---|---|
| VH CDR1 | FSLSFSGVGVA | 12 |
| VH CDR2 | LIYWDDDKRYSPSLKS | 13 |
| VH CDR3 | REWKAFGAFDI | 14 |
| VL CDR1 | SGSSSNIGSNTVN | 15 |
| VL CDR2 | NNQRPSG | 16 |
| VL CDR3 | ATWDDSLNGAV | 17 |

A similar construct with R5 antibody was made with an IL-4 fusion, as follows:

R5-IL4 (SEQ ID NO:4), where residues 268-396 is the human IL-4 protein.

R5IL4
(SEQ ID NO: 4)
ASQITLKESGPTLVKPTQTLTLTCSFSGFSLSFSGVGVAWIRQPPGKALE

WLALIYWDDDKRYSPSLKSRLTITKDTSKNQWLTMTNMDPLDTATYYCAH

REWKAFGAFDIWGQGTMVTVSSGILGSGGGSGGGGSGGGGSQPVLTQSP

SASGTPGQRVTISCSGSSSNIGSNTVNWYQQLPGTAPKLLIYSNNQRPSG

VPDRFSGSKSVTSASLAISGLQSEDEAEYYCATWDDSLNGAVFGGGTQLT

VLSGILGSGSGSGSGSHKCDITLQEIIKTLNSLTEQKTLCTELTVTDIFA

ASKNTTEKETFCRAATVLRQFYSHHEKDTRCLGATAQQFHRHKQURFLKR

LDRNLWGLAGLNSCPVKEANQSTLENFLERLKTIMREKYSKCSSAAAHHH

HHHHH

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLE 1

To generate scFv antibody fragments recognizing RNF43 and anti-ZNRF3, we selected for binders to recombinant RNF43 and ZNRF3 using a yeast display library of naïve human scFvs.

A candidate surrogate RSPO was generated by fusing the Z6 scFv to human IL2 (SEQ ID NO:1).

Z6-IL2 fusion was expressed in insect cells and purified by nickel and gel filtration chromatography. Z6-IL2 elutes as a monodisperse peak from the gel filtration column, indicating that the protein is not aggregated and has favorable biochemical behavior.

To test the signaling activity of surrogate RSPOs, we used two different reporter cell lines HEK293T SuperTOPflash (STF) cells and CD25+ HEK 293T STF cells. The HEK 293 STF cells have a stably integrated Firefly luciferase driven by 8×TCF/LEF binding sites (a Wnt responsive promoter) and constitutively expressed Renilla luciferase control reporter. The CD25+ HEK 293T STF cells were generated by using a retroviral expression system to transduce the HEK293T STF cells with human CD25 (an IL-2 receptor)

To monitor enhancement of Wnt activity, we treated STF cells or CD25+ STF cells with either Wnt3a conditioned media, or with a surrogate Wnt agonist (described previously in a different Garcia lab disclosure) in the presence or absence surrogate RSPO Z6-IL2 or control proteins. We then lysed the cells and performed a luciferase assay.

Surrogate RSPO (Z6-IL2) has modest effect on untransfected STF 293 cells treated with Wnt3a conditioned media. Z6-IL2, negative control scFv, IL2 have no effect in the absence of a Wnt agonist. Surrogate RSPO (Z6-IL2) has modest effect on untransfected STF 293 cells treated with surrogate Wnt (scFv+Dkk1). Z6-IL2, negative control scFv, IL2 have no effect in the absence of a Wnt agonist. Surrogate RSPO (Z6-IL2) has a strong effect on CD25+ cells treated with surrogate Wnt (scFv+Dkk1), indicating selectivity for the target cell type. Z6-IL2, negative control scFv, IL2 have no effect in the absence of a Wnt agonist.

We also generated fusions of the Z6 scFv to IL4, and fusions of the RNF43-binding scFv, R5, to IL2 and IL4.

EXAMPLE 2

Secreted R-spondin1-4 proteins (RSPO1-4) orchestrate intestinal stem cell renewal and tissue homeostasis by potentiating canonical Wnt signaling. RSPOs function by connecting the extracellular domains (ECDs) of negative Wnt regulators RNF43 or ZNRF3 to the co-receptors LGR4, LGR5, or LGR6, which induces membrane clearance of the complex. Although RSPOs are emerging candidates for applications in regenerative medicine, the sparse tissue distribution of LGR4/5/6 proteins limits their overall biomedical utility.

Here, we have provided bispecific ligands that potentiate Wnt activity independent of LGR4/5/6. These 'surrogate RSPOs' consist of an RNF43- or ZNRF3-specific single chain antibody variable fragment (scFv) connected to the immune cytokine IL-2 via a flexible linker. Surrogate RSPOs mimic the function of natural RSPOs by crosslinking the ECD of RNF43 or ZNRF3 to the ECD of the IL-2 receptor CD25, leading to highly selective amplification of Wnt signaling on CD25-expressing cells. Furthermore, surrogate RSPOs were able to functionally replace wild type RSPOs to stimulate the growth of CD25+ human colon organoids. These results demonstrate engineered ligands that mimic RSPO function on a broad range of cell- or tissue-types, and open new avenues for the development of RSPO-based therapeutics.

Figure 7:
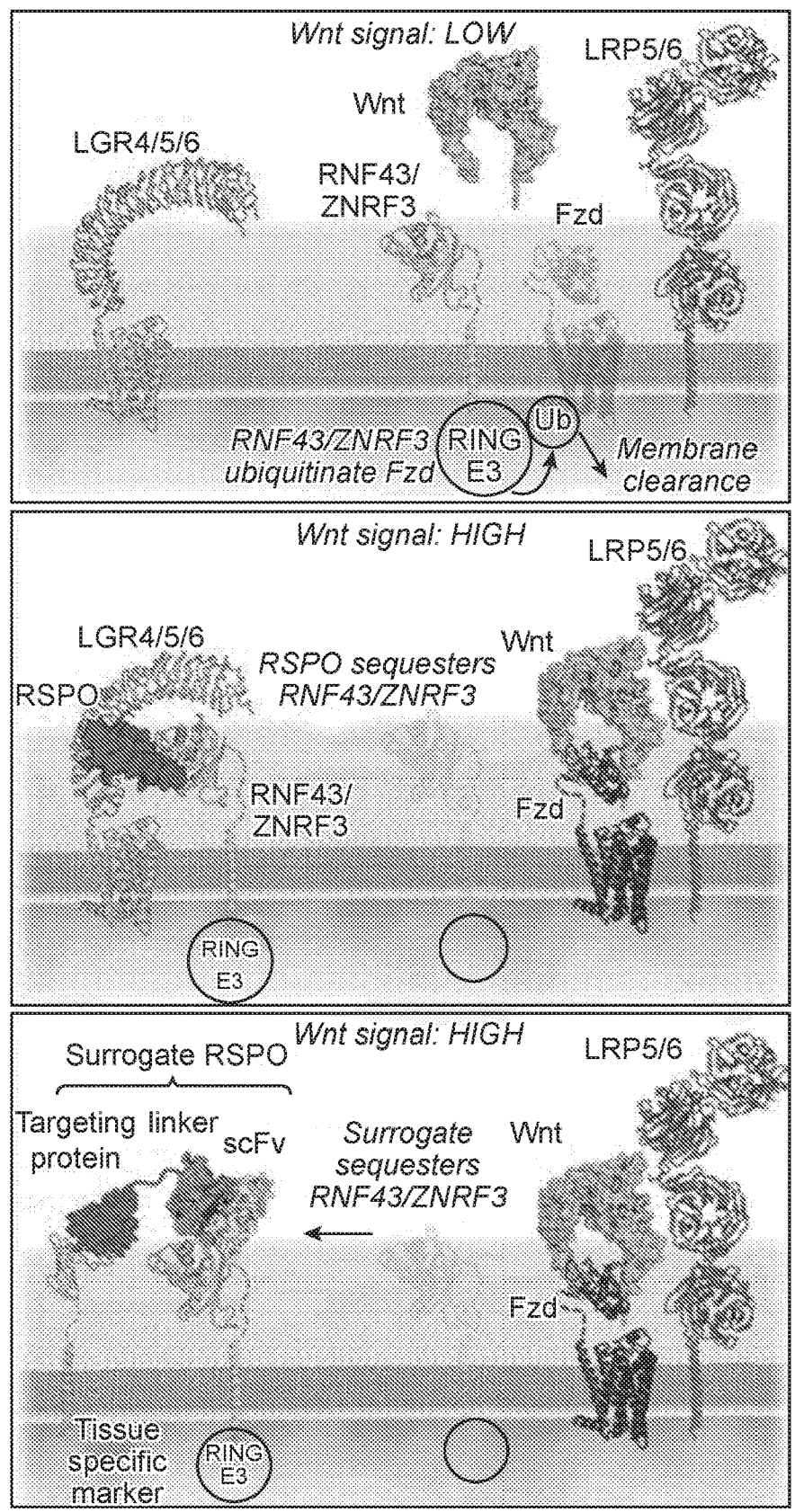
FIG. 7. The R-spondin signaling mechanism. In the absence of RSPO, ZNRF3 drives membrane clearance of Fzd receptors to negatively regulate Wnt signaling. RSPO-mediated crosslinking of the ECDs of RNF43 or ZNRF3 and LGR4, LGR5, or LGR6 sequesters RNF43/ZNRF3 to restore Fzd surface levels, thereby potentiating Wnt activity. Surrogate RSPOs mimic the function of wild type RSPOs by cross-linking RNF43 or ZNRF3 to tissue-specific markers known to undergo endocytosis upon ligand binding.

The Wnt signaling pathway controls stem cell development and tissue homeostasis in all metazoans. Wnt activity is tightly regulated by several host-encoded proteins, which can function to either potentiate or attenuate signaling. R-spondin proteins (RSPO1-4 in mammals) function by antagonizing negative regulators of the Wnt pathway, and co-administration of Wnts and RSPOs can result in signaling outputs that are several hundred-fold greater than those of Wnt alone. RSPO-mediated enhancement of Wnt activity occurs via an indirect mechanism that greatly increases levels of the Wnt receptors Frizzled (Fzd) and LRP5 or LRP6 on the cell surface. In the absence of RSPO, Wnt receptors are continuously downregulated by the transmembrane E3 ligases (TMULs) RNF43 and ZNRF3, which mediate ubiquitination of intracellular regions of Fzd to target both Fzd and associated LRP5/6 proteins for internalization and degradation (FIG. 7A). RSPOs deactivate RNF43/ZNRF3 by simultaneously binding their extracellular protease-associated (PA) domains and the extracellular domain (ECD) of a second receptor, the Leucine-rich repeat-containing G-protein coupled receptor 4, 5 or 6 (LGR4-6). Cross-linking of RNF43/ZNRF3 to LGR4/5/6 by RSPO induces membrane clearance of the ternary complex, which sequesters RNF43/ZNRF3 from Fzd and in turn potentiates Wnt signaling (FIG. 7B).

Biomedical applications of recombinant RSPOs have been widely explored in the field of regenerative medicine, especially in the context of the small intestine where RSPOs function to promote the renewal of stem cells at the base of the crypt. For example, recombinant RSPO1 protects animals from both experimentally induced colitis and from lethal doses of chemoradiation by stimulating intestinal regeneration. Furthermore, the addition of exogenous RSPO is critical for the culture of intestinal organoids, an in vitro model system used for studies of the intestinal epithelium. It was recently reported that Wnts and RSPOs play non-equivalent roles in intestinal stem cell (ISC) self-renewal through a feedback loop in which Wnts drive the expression of LGR5 and RSPOs induce ISC expansion, raising the possibility that targeting the pathways individually or in concert may be associated with unique therapeutic outcomes.

RSPOs are promising candidates selectively boost innate Wnt activity and circumvent off-target effects, yet their biomedical utility is limited by the restricted expression of LGR4/5/6 to only a small subset of cell types. To overcome the limitations of naturally encoded RSPOs, we engineered synthetic ligands that phenocopy RSPO-mediated Wnt signal enhancement via an LGR4/5/6-independent mechanism. These "surrogate RSPOs" function by cross-linking the RNF43 or ZNRF3 ECD to a cell surface marker (CD25) that is known to undergo internalization upon ligand binding, thus mimicking RSPO-mediated sequestration of RNF43/ZNRF3 (FIG. 7C). Surrogate RSPOs drive receptor-specific amplification of Wnt signaling in reporter cells and human colon organoids, and their modular design allows them to be adapted to target virtually any cell type, a feature that has major implications for the development of Wnt-based therapeutics.

Results

Figure 8D:
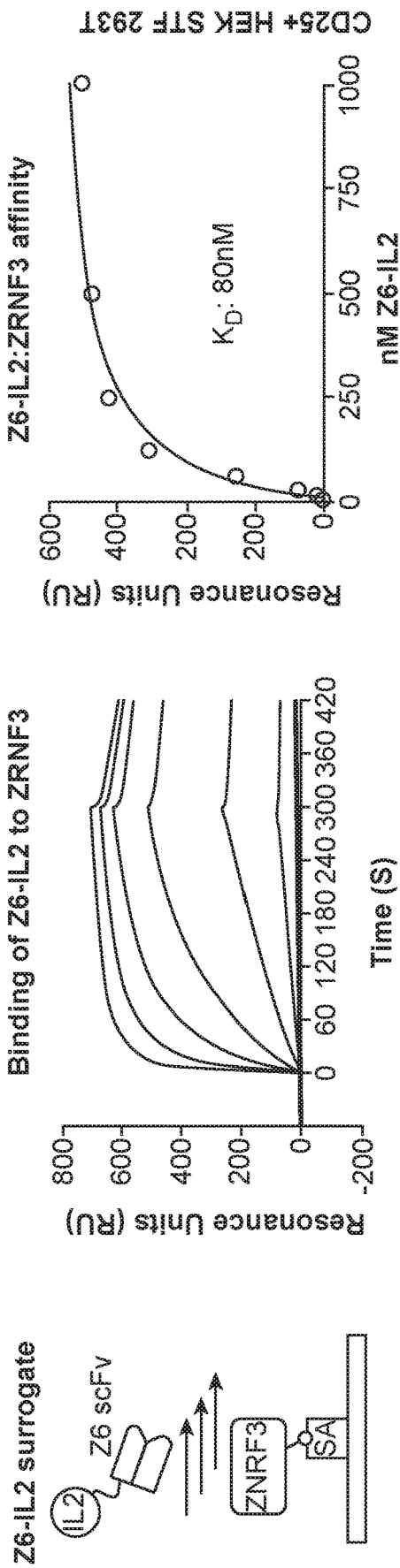

Generation of RNF43- and ZNRF3-specific scFvs. Our surrogate RSPO design utilizes the fusion of two components: (i) a RNF43- or ZNRF3-binding protein and (ii) a tissue-specific targeting protein that induces endocytosis of its receptor. Administration of the surrogate RSPO protein cross-links the ECD of RNF43 or ZNRF3 to the module's cognate receptor and mimics the function of natural RSPOs by driving membrane clearance of the complex. We isolated the RNF43- or ZNRF3-binding protein components for the surrogate RSPOs by selecting single-chain variable fragments (scFvs) from a published yeast display library of ~1×10$^9$ sequences derived from human B-cells. The scFvs were obtained by performing two parallel sets of selections against either the RNF43 ECD or the ZNRF3 ECD using either magnetic activated cell sorting (MACS) or fluorescence activated cell sorting (FACS). After several rounds of selections, we isolated a panel of different RNF43- or ZNRF3-specific scFvs (FIG. 11), and the clones "R5" and "Z6" were chosen for incorporation into the surrogate RSPO cassette based on their ability to robustly bind to RNF43 and ZNRF3, respectively, in a fluorescence-based assay (FIG. 8A).

Figure 11:
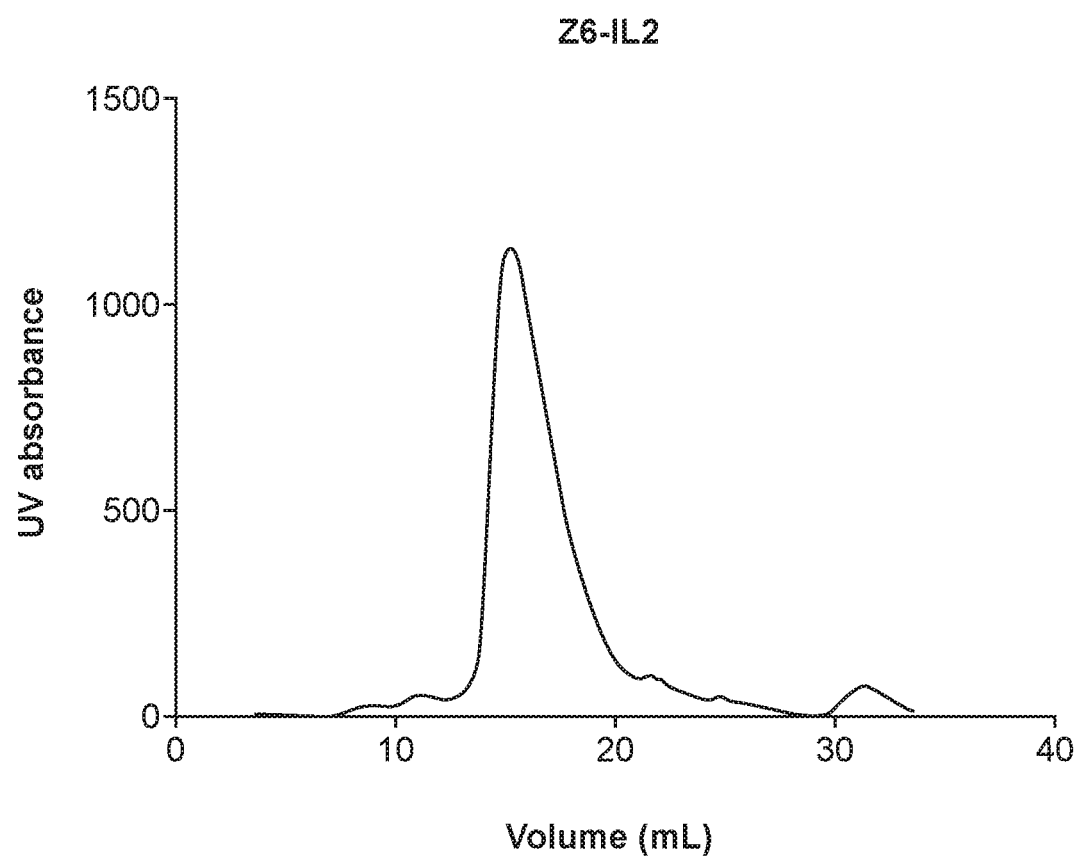
FIG. 11. R5-IL2 and Z6-IL2 proteins elute as monodisperse peaks from gel filtration columns. The $UV_{280}$ absorbance from the gel filtration elution profiles of R5-IL2 (left) and Z6-IL2 (right) $UV_{280}$ absorbance are depicted.

Design, expression and purification of surrogate RSPOs. Membrane clearance of RSPO signaling complexes has been reported to require the internalization of the receptors LGR4-6. We therefore selected the immune cytokine IL-2 to act as a proxy for RSPO-LGR binding in our surrogate RSPO constructs based on its ability to induce endocytosis of its cognate receptor, CD25. We generated two surrogate RSPO constructs, one targeted to RNF43 and one targeted to ZNRF3, by fusing R5 to IL-2 (R5-IL2) and Z6 to IL-2 (Z6-IL2). Single-chain constructs were designed such that R5 or Z6 is connected to the N-terminus of IL-2 via a flexible 5×(Gly-Ser) linker intended to allow R5/Z6 and IL-2 to independently bind their respective targets. R5-IL2 and Z6-IL2 were expressed in insect cells using baculovirus and both proteins eluted as monodisperse peaks from a gel filtration column, which is indicative of favorable biochemical behavior (FIG. 11).

Biophysical characterization of surrogate RSPO-receptor interactions. We used surface plasmon resonance (SPR) to measure the binding affinity of R5-IL2 and Z6-IL2 for RNF43 and ZNRF3. We determined that R5-IL2 bound to RNF43 with a dissociation constant ($K_d$) of 58 nM, and that Z6-IL2 bound to ZNRF3 with a $K_d$ of 80 nM. R5-IL2 did not cross-react with ZNRF3, and Z6-IL2 did not cross-react with RNF43. We also used SPR to determine that R5-IL2 and Z6-IL2 bound to CD25 with Kd values nearly identical to the reported $K_d$ of the wild type CD25-IL2 interaction. Collectively, our SPR experiments revealed that R5 and Z6 bind to their respective targets with similar affinities, that the affinities of surrogate RSPOs fall within the range of those reported between wild type RSPOs and RNF43/ZNRF3 (~5-10,000 nM), and that that IL-2 binding to CD25 is retained in the surrogate RSPO format.

Figure 9A:
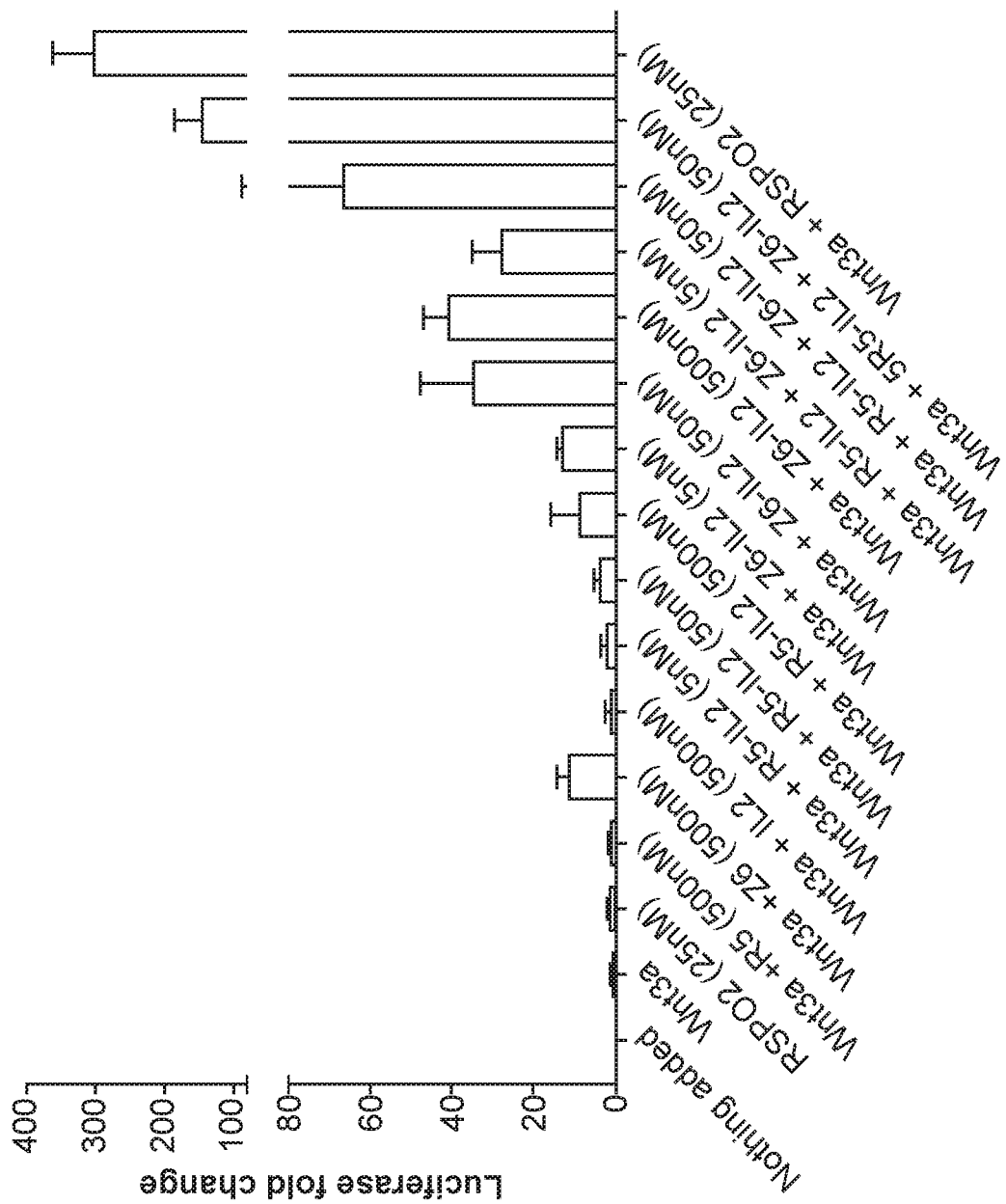
FIG. 9. Surrogate RSPOs potentiate Wnt signaling. (A) Luciferase reporter assay measuring surrogate RSPO potentiation of Wnt activity in CD25-expressing cells. HEK STF 293T cells lentivirally transduced with CD25 were incubated with various recombinant proteins in the presence of 20% Wnt3a conditioned media. (B) A reporter assay was performed under the same conditions as in (A) using uninfected (CD25 negative) HEK STF 293T cells.

Surrogate RSPO-mediated enhancement of Wnt signaling. We performed a luciferase assay to test the ability of R5-IL2 and Z6-IL2 to selectively potentiate Wnt signaling. We compared the activity of surrogate RSPOs on HEK 293 Super Top Flash (STF) Wnt reporter cells, or on HEK 293 STF cells that had been lentivirally transduced with CD25. In the CD25-expressing cells, R5-IL2 increased Wnt3a reporter activity up to 9.5-fold, and Z6-IL2 increased Wnt3a activity up to 41-fold (FIG. 9A). The greater activity of Z6-IL2 relative to R5-IL2 is consistent with a previous report that found ZNRF3 to be the dominantly expressed homolog (relative to RNF43) in HEK 293 cells. Given that natural RSPOs are cross-reactive, and that sequestration of both RNF43 and ZNRF3 may be required for the potent activity of RSPO2, we posited that the combination of R5-IL2 and Z6-IL2 would have a synergistic effect. We therefore incubated the cells with a 1:1 mixture of R5-IL2 and Z6-IL2 and found that this combination increased Wnt3a activity by 148-fold (FIG. 9A). In the untransduced cells, addition of R5-IL2, Z6-IL2, and R5-IL2+Z6-IL2 led to increases in Wnt3a activity of only 2.7, 3.9 and 5.8-fold, respectively (FIG. 9B), indicating that surrogate RSPO activity is highly selective for cells expressing CD25.

Figure 9B:
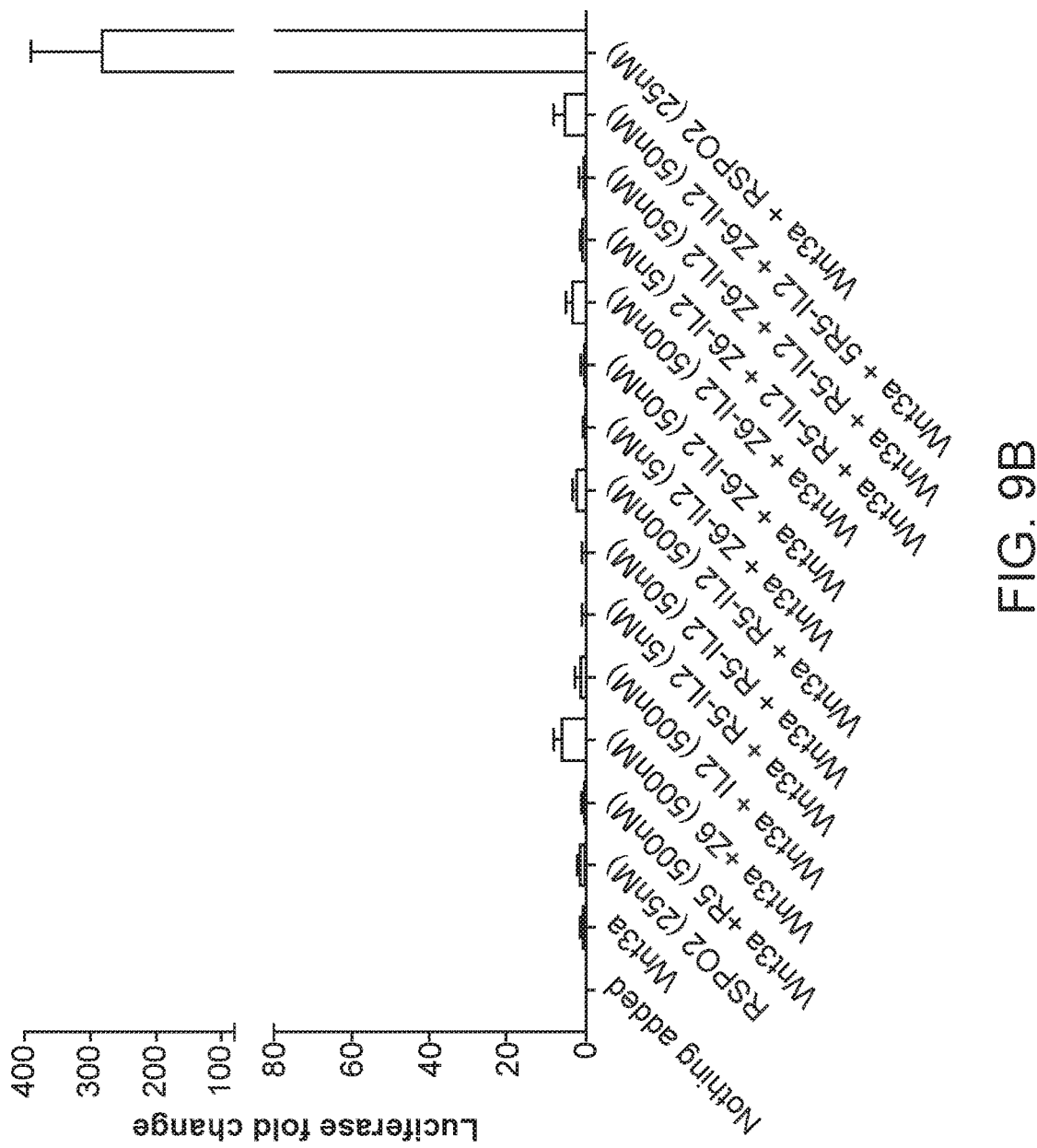

In both CD25 positive and CD25 negative cells, we found that a mixture of conditioned Wnt3a media and the receptor-binding fragment of RSPO2 (Furin domains 1 and 2) elicited a response that was 286- to 304-fold greater than that of Wnt3a alone (FIGS. 9A, 9B), which is similar to previously observed levels of RSPO-mediated enhancement. As a negative control, we treated cells with Wnt3a conditioned media supplemented with either R5, Z6, or IL-2. The R5 scFv and IL2 cytokine did not substantially potentiate Wnt3a signaling (FIG. 9B). However, the Z6 scFv exhibited mild agonist activity that resulted in 10-fold or 12-fold increases in signaling in the HEK293 STF and CD25-expressing cells, respectively (FIG. 9A, 9B).

Figure 10:
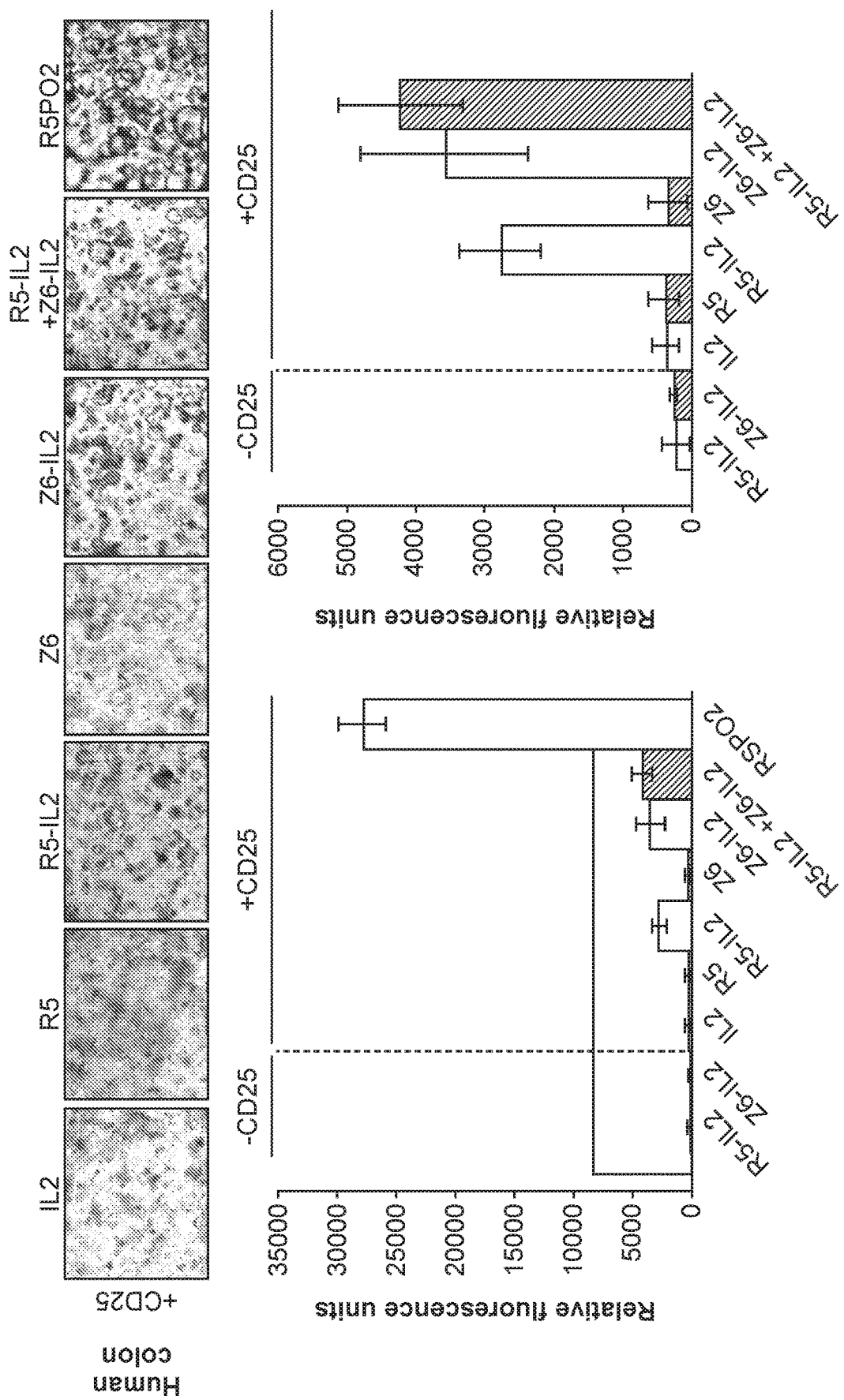
FIG. 10. Surrogate RSPOs stimulate intestinal organoid growth. Surrogate RSPOs were tested for their ability to stimulate the growth of LGR5+ human colon organoids that had been lentivirally transduced to express CD25. Media lacking RSPO2 was supplemented with 500 nM concentrations of the indicated proteins and organoid growth was monitored by microscopy (top) and fluorescence (bar graphs, bottom). The bar graph on the right is a zoomed panel of the colored region from the graph on the left.

Surrogate RSPO-mediated stimulation of intestinal organoid growth. Differentiation of stem cells into human colon organoids requires the addition of exogenous RSPO along with Wnt, EGF, Noggin, and TGF-β inhibitor. To determine whether R5-IL2 or Z6-IL2 can substitute for RSPO in human colon organoid culture, we performed an organoid growth assay using LGR5+ intestinal stem cells had been lentivirally transduced to express CD25. In this assay, CD25+ stem cells were cultured in the presence of RSPO, IL-2, R5 scFv, Z6 scFv, R5-IL2, Z6-IL2, or a 1:1 mixture of R5-IL2 and Z6-IL2, and organoid growth was monitored by fluorescence. We found that addition of R5-IL2, Z6-IL2, or the mixture of R5-IL2 and Z6-IL2 each led to significant increases in organoid growth relative to our negative control protein, IL-2 (FIG. 10). Addition of either the R5 scFv or Z6 scFv, on the other hand, did not result in a significant increase. Fluorescence was increased by 7.3-fold in R5-IL2 treated cultures, by 9.4-fold in Z6-IL2 treated cultures, and by 11-fold in cultures treated with the mixture of R5-IL2 and Z6-IL2. Our positive control RSPO2 stimulated growth by 73-fold, and exhibited a stronger effect than the mixture of R5-IL2 and Z6-IL2, which is similar to what we observed in our luciferase assay. Importantly, neither R5-IL2 nor Z6-IL2 stimulated the growth of wild type organoids (FIG. 10), indicating that surrogate RSPOs specifically affect cells expressing the target receptor of CD25.

The development of surrogate RSPO proteins represents a new method for facilitating tissue-specific potentiation of Wnt activity and has expanded our understanding of the RSPO signaling mechanism. Here, we have shown that surrogate RSPOs can mimic the activity of endogenous RSPOs in the absence of cognate LGR4/5/6 receptor by coopting IL-2 ligands known to induce endocytosis of the CD25 receptor. This finding supports the present model that RSPOs function by driving endocytosis of RNF43/ZNRF3 and opens new avenues for the engineering surrogate RSPOs that act upon a broad spectrum of endocytosable receptors. Notably, the strongest Wnt signal potentiation in 293 cells was achieved by co-administering the R5-IL2 and Z6-IL2 surrogate RSPOs (FIG. 9), indicating that the inherent cross-reactivity of natural RSPOs allows them to overcome inhibition both RNF43- and ZNRF3-mediated inhibition. Optimization of surrogate RSPOs may therefore be achieved by incorporating cross-reactive RNF43/ZNRF3 binding modules, such as the RSPO FU1 domain, into the design. On the other hand, the ability of the existing surrogate RSPOs to target a given E3 ligase (RNF43 versus ZNRF3) confers an additional degree of selectivity that may be beneficial in certain contexts.

Materials and Methods

Protein expression and purification. Human RNF43 Extracellular Domain (ECD) (amino acids 24-197) and ZNRF3 ECD (amino acids 56-219) were cloned into the pAcGp67A vector with a C-terminal biotin-acceptor peptide tag (SEQ ID NO:5, GLNDIFEAQKIEW) followed by 6×His tag. Unless otherwise specified, RNF43/ZNRF3 in the method section will refer to their ECD only. Selected RNF43 and ZNRF3 high-affinity human antibody scFv fragments were cloned into pAcGp67A with a C-terminal 6×His tag. These human antibody scFv fragments were also cloned into pAcGp67A in frame with a $(GS)_5$ linker and human interleukin-2 (amino acids 21-153) followed by 6×His tag. All proteins were expressed in Hi-Five cells (Invitrogen) from Trichoplusiani infected with Baculovirus. The cultures were harvested 60 hours after infection. Proteins were purified by nickel affinity chromatography followed by size exclusion chromatography in 1×HBS buffer (10 mM HEPES pH 7.2, 150 mM sodium chloride). RNF43 and ZNRF3 were site-specifically biotinylated by BirA ligase at the C-terminal biotin-acceptor peptide prior to size-exclusion chromatography. This size-exclusion chromatography is to eliminate free biotin in the buffer. All proteins were either used when freshly purified or snap frozen in liquid nitrogen with 20% glycerol.

Selection of RNF43/ZNRF3-binding scFv fragments. The nonimmune yeast surface display library of human antibody scFv fragments was generously provided by the Wittrup group (Feldhaus et al. Flow-cytometric isolation of human antibodies from a nonimmune Saccharomyces cerevisiae surface display library. Nature biotechnology 21, 163 (2003)). A sequential selection strategy by magnetic bead selection followed by flow-cytometric sorting was used as previously reported (Luca et al. Structural basis for Notch1 engagement of Delta-like 4. Science 347, 847-853 (2015)). The selection round 1 was performed by first mixing 250 uL magnetic streptavidin microbeads (Militenyi) with 400 nM biotinylated RNF43/ZNRF3. These microbeads were further mixed with $1 \times 10^{10}$ yeast from the scFv fragment library. Yeast were subsequently flown through a Magnetic-Activated cell sorting (MACS) LS separation column (Militenyi) to collect ZNRF3/RNF43 binders. Round 2 was performed by repeating round 1 using $1 \times 10^8$ yeasts from the collected fractions. In round 3, yeast were pre-incubated with 200 nM biotinylated RNF43/ZNRF3 prior to incubation with Alexafluor-647 dye (SA-647, Life Technologies). The ZNRF3/RNF43 binders were enriched using anti-647 microbeads (Militenyi) by MACS. In round 4, yeast were pre-incubated with 5 nM biotinylated RNF43 or 10 nM biotinylated ZNRF3. The yeast were further stained by SA-647 and Alexa Fluor 488-conjugated antibody to the c-Myc epitope (Myc-488, Cell Signaling). The high-affinity RNF43/ZNRF3 binders were isolated by fluorescence-activated cell sorting (FACS).

Plasmids from the final round of selection were isolated using the Zymoprep Yeast Plasmid Miniprep Kit (Zymo Research) and sequenced. These plasmids were electroporated into S. cerevisiae EBY100 yeast and recovered in SDCAA selection media, followed by induction in SGCAA induction media. The individual scFv-transformed yeast were incubated with increasing concentration of biotinylated RNF43/ZNRF3. These yeast were stained with SA-647 and Myc-488 and fluorescence was monitored by flow cytometry. The data were analyzed by GraphPad Prism 7 and the highest affinity clones were identified for subsequent experiments.

Binding of RNF43 and ZNRF3 to yeast surface displayed scFvs. Yeast cells expressing either the R5 or Z6 scFvs were stained with 1 μM concentrations of recombinant RNF43 or ZNR3 ECDs, respectively in PBS+0.1% BSA. Cells were then washed, and incubated with SA-647 and Myc-488, washed again, and then analyzed by flow cytometry.

Surface plasmon resonance. All binding measurements were conducted using a BIAcore T100 instrument (GE Healthcare). Biotinylated RNF43, ZNRF3 and CD25 were coupled on a SA sensor chip (GE Healthcare) at low density. An unrelated biotinylated protein was captured at equivalent coupling density to the control flow cells. Increasing concentrations of R5-IL2 and Z6-IL2 were injected onto the chip in HBS-P (GE Healthcare) at 30 μl/mL. Resonance units were calculated by subtracting the resonance units observed in RNF43, ZNRF3, or CD25-containing flow cells from those of the control flow cell. Curves were fitted to a 1:1 binding model using the Biaevaluation software (Biacore/GE Healthcare).

Luciferase signaling assays. HEK293 cells were previously stably transfected with Firefly Luciferase Reporter under the control of a concatemer of seven LEF/TCF binding sites and Renilla Luciferase Reporter by lentivirus as described by Janda et al. Surrogate Wnt agonists that phenocopy canonical Wnt and β-catenin signalling. *Nature* 545, 234-237 (2017). These cells were further stably transfected with human CD25 with retrovirus, which co-express YFP. Transfected HEK293 cells were FACS sorted by YFP expression. CD25 surface expression were further confirmed by staining the transfected HEK293 cells with Brilliant Violet 605 antibody (BioLegend, Clone BC96, #302632). Fluorescence was monitored by flow cytometry and was compared to non-transfected HEK293 cells. The Dual Luciferase assays were conducted using the Dual Luciferase Assay kit (Promega) as instructed. Briefly, cells were plated at a density of 10,000 cells per well to a 96-well plate 24 hours prior to stimulation. Cells were stimulated with 20% Wnt3A conditioned media (ATCC) supplemented with RSPO2 protein or surrogate RSPO. Cells were cultured in the presence of stimulation reagents for another 24 hours before washed and lysed as in the Dual Luciferase Assay kit (Promega) manual. Luminance signals were recorded using SpectraMax Paradigm and analyzed by GraphPad Prism 7.

Organoid growth assays. Fresh colonic samples were collected at Stanford Hospital with informed consent. The culture was passaged several times in WENR media (Wnt3a, R-spondin, EGF, Noggin) to confirm robust outgrowth of organoids. To evaluate surrogate activity, the organoids were transduced with lentivirus expressing CD25 and FACS sorted for YFP+ (YFP co-expression with CD25) to enrich CD25+ population. CD25+ cells were subcultured in media conditioned as in FIG. 10. Organoids morphology were observed and phase contrast pictures were taken using Nikon TS100. To quantify cell growth, organoids were dissociated to single cells are plated at 10,000 cells per well in 96-well format. Cell viability assay was performed 3 days after plating using alamarBlue cell viability reagent (Thermo Fisher).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. An RSPO surrogate composition that comprises:
   (i) a specific binding domain for RNF43 or ZNRF3, wherein the specific binding domain for RNF43 or ZNRF3 is an antibody or antigen-binding fragment thereof; and
   (ii) a cell-targeting domain, wherein the cell-targeting domain is a cytokine or growth factor that specifically binds a cell surface receptor.

2. The composition of claim 1, wherein the specific binding domain for RNF43 or ZNRF3 comprises 6 CDR sequences of Z6 or R5 binding sequences set forth in any one of SEQ ID NO:1-4.

3. The composition of claim 1, wherein the specific binding domain for RNF43 or ZNRF3 is a single-chain Fv (scFv) construct.

4. The composition of claim 1, wherein the cell-targeting domain is the or growth factor.

5. The composition of claim 4, wherein the cell-targeting domain is the cytokine.

6. The composition of claim 5, wherein the cytokine is IL-2 or IL-4.

7. The composition of claim 1, wherein the domains are fused through a flexible linker.

8. The composition of claim 1, wherein the domains are directly joined.

9. The composition of claim 1, formulated with an effective dose of a Wnt agent.

10. The composition of claim 1, joined to a Wnt agent.

* * * * *

SEQUENCE LISTING

```
<160> NUMBER OF SEQ ID NOS: 18

<210> SEQ ID NO 1
<211> LENGTH: 408
<212> TYPE: PRT
<213> ORGANISM: Artificial sequence
<220> FEATURE:
<223> OTHER INFORMATION: synthetic polypeptide

<400> SEQUENCE: 1

Ala Ser Gln Val Gln Leu Val Gln Ser Gly Ala Glu Val Lys Asn Pro
1               5                   10                  15

Gly Ala Ser Val Lys Val Ser Cys Lys Ala Ser Gly Tyr Ala Phe Thr
            20                  25                  30

Ser Tyr Gly Ile Ser Trp Val Arg Gln Ala Pro Gly Gln Gly Leu Glu
        35                  40                  45

Trp Met Gly Trp Ile Ser Ala Tyr Thr Arg Asn Thr Asn Tyr Ala Gln
    50                  55                  60

Lys Phe Gln Gly Arg Val Thr Leu Thr Thr Asp Thr Ser Thr Ser Thr
65                  70                  75                  80
```

Ala Tyr Met Glu Leu Arg Ser Leu Arg Ser Asp Asp Thr Ala Ile Tyr
                85                  90                  95

Tyr Cys Ala Arg Asp Ala Arg Tyr Ser Leu Gly Val Gly Ala Phe Asp
            100                 105                 110

Val Trp Gly Gln Gly Thr Met Val Thr Val Ser Ser Gly Ile Leu Gly
        115                 120                 125

Ser Gly Gly Gly Ser Gly Gly Gly Ser Gly Gly Gly Gly Ser
130                 135                 140

Glu Thr Thr Leu Thr Gln Ser Pro Ala Phe Met Ser Ala Thr Pro Gly
145                 150                 155                 160

Asp Lys Val Ser Ile Ser Cys Lys Ala Ser Arg Asp Ile Asp Asp Asp
                165                 170                 175

Leu Asn Trp Tyr Gln Gln Lys Pro Gly Glu Ala Ala Ile Ser Ile Ile
            180                 185                 190

Gln Glu Ala Thr Thr Leu Val Pro Gly Ile Pro Pro Arg Phe Ser Gly
        195                 200                 205

Ser Gly Tyr Gly Thr Asp Phe Thr Leu Thr Ile Asn Asn Ile Glu Ser
    210                 215                 220

Glu Asp Ala Ala Tyr Tyr Phe Cys Leu Gln His Asp Asp Val Pro Tyr
225                 230                 235                 240

Thr Phe Gly Gln Gly Thr Lys Leu Glu Ile Lys Ser Gly Ile Leu Gly
                245                 250                 255

Ser Gly Ser Gly Ser Gly Ser Gly Ser Ala Pro Thr Ser Ser Ser Thr
            260                 265                 270

Lys Lys Thr Gln Leu Gln Leu Glu His Leu Leu Leu Asp Leu Gln Met
        275                 280                 285

Ile Leu Asn Gly Ile Asn Asn Tyr Lys Asn Pro Lys Leu Thr Arg Met
    290                 295                 300

Leu Thr Phe Lys Phe Tyr Met Pro Lys Lys Ala Thr Glu Leu Lys His
305                 310                 315                 320

Leu Gln Cys Leu Glu Glu Glu Leu Lys Pro Leu Glu Glu Val Leu Asn
                325                 330                 335

Leu Ala Gln Ser Lys Asn Phe His Leu Arg Pro Arg Asp Leu Ile Ser
            340                 345                 350

Asn Ile Asn Val Ile Val Leu Glu Leu Lys Gly Ser Glu Thr Thr Phe
    355                 360                 365

Met Cys Glu Tyr Ala Asp Glu Thr Ala Thr Ile Val Glu Phe Leu Asn
370                 375                 380

Arg Trp Ile Thr Phe Cys Gln Ser Ile Ile Ser Thr Leu Thr Ala Ala
385                 390                 395                 400

Ala His His His His His His
            405

<210> SEQ ID NO 2
<211> LENGTH: 405
<212> TYPE: PRT
<213> ORGANISM: Artificial sequence
<220> FEATURE:
<223> OTHER INFORMATION: synthetic polypeptide

<400> SEQUENCE: 2

Ala Ser Gln Val Gln Leu Val Gln Ser Gly Ala Glu Val Lys Asn Pro
1               5                   10                  15

Gly Ala Ser Val Lys Val Ser Cys Lys Ala Ser Gly Tyr Ala Phe Thr
            20                  25                  30

```
Ser Tyr Gly Ile Ser Trp Val Arg Gln Ala Pro Gly Gln Gly Leu Glu
         35                  40                  45

Trp Met Gly Trp Ile Ser Ala Tyr Thr Arg Asn Thr Asn Tyr Ala Gln
 50                  55                  60

Lys Phe Gln Gly Arg Val Thr Leu Thr Thr Asp Thr Ser Thr Ser Thr
 65                  70                  75                  80

Ala Tyr Met Glu Leu Arg Ser Leu Arg Ser Asp Asp Thr Ala Ile Tyr
                 85                  90                  95

Tyr Cys Ala Arg Asp Ala Arg Tyr Ser Leu Gly Val Gly Ala Phe Asp
                100                 105                 110

Val Trp Gly Gln Gly Thr Met Val Thr Val Ser Ser Gly Ile Leu Gly
            115                 120                 125

Ser Gly Gly Gly Ser Gly Gly Gly Ser Gly Gly Gly Ser
130                 135                 140

Glu Thr Thr Leu Thr Gln Ser Pro Ala Phe Met Ser Ala Thr Pro Gly
145                 150                 155                 160

Asp Lys Val Ser Ile Ser Cys Lys Ala Ser Arg Asp Ile Asp Asp Asp
                165                 170                 175

Leu Asn Trp Tyr Gln Gln Lys Pro Gly Glu Ala Ala Ile Ser Ile Ile
            180                 185                 190

Gln Glu Ala Thr Thr Leu Val Pro Gly Ile Pro Pro Arg Phe Ser Gly
            195                 200                 205

Ser Gly Tyr Gly Thr Asp Phe Thr Leu Thr Ile Asn Asn Ile Glu Ser
210                 215                 220

Glu Asp Ala Ala Tyr Tyr Phe Cys Leu Gln His Asp Asp Val Pro Tyr
225                 230                 235                 240

Thr Phe Gly Gln Gly Thr Lys Leu Glu Ile Lys Ser Gly Ile Leu Gly
                245                 250                 255

Ser Gly Ser Gly Ser Gly Ser Gly Ser His Lys Cys Asp Ile Thr Leu
            260                 265                 270

Gln Glu Ile Ile Lys Thr Leu Asn Ser Leu Thr Glu Gln Lys Thr Leu
            275                 280                 285

Cys Thr Glu Leu Thr Val Thr Asp Ile Phe Ala Ala Ser Lys Asn Thr
290                 295                 300

Thr Glu Lys Glu Thr Phe Cys Arg Ala Ala Thr Val Leu Arg Gln Phe
305                 310                 315                 320

Tyr Ser His His Glu Lys Asp Thr Arg Cys Leu Gly Ala Thr Ala Gln
                325                 330                 335

Gln Phe His Arg His Lys Gln Leu Ile Arg Phe Leu Lys Arg Leu Asp
            340                 345                 350

Arg Asn Leu Trp Gly Leu Ala Gly Leu Asn Ser Cys Pro Val Lys Glu
355                 360                 365

Ala Asn Gln Ser Thr Leu Glu Asn Phe Leu Glu Arg Leu Lys Thr Ile
370                 375                 380

Met Arg Glu Lys Tyr Ser Lys Cys Ser Ser Ala Ala His His
385                 390                 395                 400

His His His His His
            405

<210> SEQ ID NO 3
<211> LENGTH: 411
<212> TYPE: PRT
<213> ORGANISM: Artificial sequence
<220> FEATURE:
```

<223> OTHER INFORMATION: synthetic polypeptide

<400> SEQUENCE: 3

```
Ala Ser Gln Ile Thr Leu Lys Glu Ser Gly Pro Thr Leu Val Lys Pro
1               5                   10                  15

Thr Gln Thr Leu Thr Leu Thr Cys Ser Phe Ser Gly Phe Ser Leu Ser
            20                  25                  30

Phe Ser Gly Val Gly Val Ala Trp Ile Arg Gln Pro Pro Gly Lys Ala
        35                  40                  45

Leu Glu Trp Leu Ala Leu Ile Tyr Trp Asp Asp Asp Lys Arg Tyr Ser
    50                  55                  60

Pro Ser Leu Lys Ser Arg Leu Thr Ile Thr Lys Asp Thr Ser Lys Asn
65                  70                  75                  80

Gln Val Val Leu Thr Met Thr Asn Met Asp Pro Leu Asp Thr Ala Thr
                85                  90                  95

Tyr Tyr Cys Ala His Arg Glu Trp Lys Ala Phe Gly Ala Phe Asp Ile
            100                 105                 110

Trp Gly Gln Gly Thr Met Val Thr Val Ser Ser Gly Ile Leu Gly Ser
        115                 120                 125

Gly Gly Gly Gly Ser Gly Gly Gly Ser Gly Gly Gly Gly Ser Gln
130                 135                 140

Pro Val Leu Thr Gln Ser Pro Ser Ala Ser Gly Thr Pro Gly Gln Arg
145                 150                 155                 160

Val Thr Ile Ser Cys Ser Gly Ser Ser Asn Ile Gly Ser Asn Thr
                165                 170                 175

Val Asn Trp Tyr Gln Gln Leu Pro Gly Thr Ala Pro Lys Leu Leu Ile
            180                 185                 190

Tyr Ser Asn Asn Gln Arg Pro Ser Gly Val Pro Asp Arg Phe Ser Gly
            195                 200                 205

Ser Lys Ser Val Thr Ser Ala Ser Leu Ala Ile Ser Gly Leu Gln Ser
    210                 215                 220

Glu Asp Glu Ala Glu Tyr Tyr Cys Ala Thr Trp Asp Asp Ser Leu Asn
225                 230                 235                 240

Gly Ala Val Phe Gly Gly Gly Thr Gln Leu Thr Val Leu Ser Gly Ile
                245                 250                 255

Leu Gly Ser Gly Ser Gly Ser Gly Ser Gly Ala Pro Thr Ser Ser
            260                 265                 270

Ser Thr Lys Lys Thr Gln Leu Gln Leu Glu His Leu Leu Leu Asp Leu
    275                 280                 285

Gln Met Ile Leu Asn Gly Ile Asn Asn Tyr Lys Asn Pro Lys Leu Thr
290                 295                 300

Arg Met Leu Thr Phe Lys Phe Tyr Met Pro Lys Lys Ala Thr Glu Leu
305                 310                 315                 320

Lys His Leu Gln Cys Leu Glu Glu Leu Lys Pro Leu Glu Glu Val
            325                 330                 335

Leu Asn Leu Ala Gln Ser Lys Asn Phe His Leu Arg Pro Arg Asp Leu
            340                 345                 350

Ile Ser Asn Ile Asn Val Ile Val Leu Glu Leu Lys Gly Ser Glu Thr
            355                 360                 365

Thr Phe Met Cys Glu Tyr Ala Asp Glu Thr Ala Thr Ile Val Glu Phe
            370                 375                 380

Leu Asn Arg Trp Ile Thr Phe Cys Gln Ser Ile Ile Ser Thr Leu Thr
385                 390                 395                 400
```

Ala Ala Ala His His His His His His
              405             410

<210> SEQ ID NO 4
<211> LENGTH: 407
<212> TYPE: PRT
<213> ORGANISM: Artificial sequence
<220> FEATURE:
<223> OTHER INFORMATION: synthetic polypeptide

<400> SEQUENCE: 4

Ala Ser Gln Ile Thr Leu Lys Glu Ser Gly Pro Thr Leu Val Lys Pro
1               5                   10                  15

Thr Gln Thr Leu Thr Leu Thr Cys Ser Phe Ser Gly Phe Ser Leu Ser
            20                  25                  30

Phe Ser Gly Val Gly Val Ala Trp Ile Arg Gln Pro Pro Gly Lys Ala
        35                  40                  45

Leu Glu Trp Leu Ala Leu Ile Tyr Trp Asp Asp Lys Arg Tyr Ser
    50                  55                  60

Pro Ser Leu Lys Ser Arg Leu Thr Ile Thr Lys Asp Thr Ser Lys Asn
65              70                  75                  80

Gln Val Val Leu Thr Met Thr Asn Met Asp Pro Leu Asp Thr Ala Thr
                85                  90                  95

Tyr Tyr Cys Ala His Arg Glu Trp Lys Ala Phe Gly Ala Phe Asp Ile
            100                 105                 110

Trp Gly Gln Gly Thr Met Val Thr Val Ser Ser Gly Ile Leu Gly Ser
        115                 120                 125

Gly Gly Gly Gly Ser Gly Gly Gly Ser Gly Gly Gly Gly Ser Gln
    130                 135                 140

Pro Val Leu Thr Gln Ser Pro Ser Ala Ser Gly Thr Pro Gly Gln Arg
145                 150                 155                 160

Val Thr Ile Ser Cys Ser Gly Ser Ser Asn Ile Gly Ser Asn Thr
                165                 170                 175

Val Asn Trp Tyr Gln Gln Leu Pro Gly Thr Ala Pro Lys Leu Leu Ile
            180                 185                 190

Tyr Ser Asn Asn Gln Arg Pro Ser Gly Val Pro Asp Arg Phe Ser Gly
        195                 200                 205

Ser Lys Ser Val Thr Ser Ala Ser Leu Ala Ile Ser Gly Leu Gln Ser
    210                 215                 220

Glu Asp Glu Ala Glu Tyr Tyr Cys Ala Thr Trp Asp Asp Ser Leu Asn
225                 230                 235                 240

Gly Ala Val Phe Gly Gly Gly Thr Gln Leu Thr Val Leu Ser Gly Ile
                245                 250                 255

Leu Gly Ser Gly Ser Gly Ser Gly Ser His Lys Cys Asp Ile
            260                 265                 270

Thr Leu Gln Glu Ile Ile Lys Thr Leu Asn Ser Leu Thr Glu Gln Lys
        275                 280                 285

Thr Leu Cys Thr Glu Leu Thr Val Thr Asp Ile Phe Ala Ala Ser Lys
    290                 295                 300

Asn Thr Thr Glu Lys Glu Thr Phe Cys Arg Ala Ala Thr Val Leu Arg
305                 310                 315                 320

Gln Phe Tyr Ser His His Glu Lys Asp Thr Arg Cys Leu Gly Ala Thr
                325                 330                 335

Ala Gln Gln Phe His Arg His Lys Gln Leu Ile Arg Phe Leu Lys Arg
            340                 345                 350

```
Leu Asp Arg Asn Leu Trp Gly Leu Ala Gly Leu Asn Ser Cys Pro Val
        355                 360                 365

Lys Glu Ala Asn Gln Ser Thr Leu Glu Asn Phe Leu Glu Arg Leu Lys
    370                 375                 380

Thr Ile Met Arg Glu Lys Tyr Ser Lys Cys Ser Ser Ala Ala Ala His
385                 390                 395                 400

His His His His His His
                405
```

```
<210> SEQ ID NO 5
<211> LENGTH: 13
<212> TYPE: PRT
<213> ORGANISM: Artificial sequence
<220> FEATURE:
<223> OTHER INFORMATION: synthetic polypeptide

<400> SEQUENCE: 5

Gly Leu Asn Asp Ile Phe Glu Ala Gln Lys Ile Glu Trp
1               5                   10
```

```
<210> SEQ ID NO 6
<211> LENGTH: 9
<212> TYPE: PRT
<213> ORGANISM: Artificial sequence
<220> FEATURE:
<223> OTHER INFORMATION: synthetic polypeptide

<400> SEQUENCE: 6

Tyr Ala Phe Thr Ser Tyr Gly Ile Ser
1               5
```

```
<210> SEQ ID NO 7
<211> LENGTH: 17
<212> TYPE: PRT
<213> ORGANISM: Artificial sequence
<220> FEATURE:
<223> OTHER INFORMATION: synthetic polypeptide

<400> SEQUENCE: 7

Trp Ile Ser Ala Tyr Thr Arg Asn Thr Asn Tyr Ala Gln Lys Phe Gln
1               5                   10                  15

Gly
```

```
<210> SEQ ID NO 8
<211> LENGTH: 13
<212> TYPE: PRT
<213> ORGANISM: Artificial sequence
<220> FEATURE:
<223> OTHER INFORMATION: synthetic polypeptide

<400> SEQUENCE: 8

Asp Ala Arg Tyr Ser Leu Gly Val Gly Ala Phe Asp Val
1               5                   10
```

```
<210> SEQ ID NO 9
<211> LENGTH: 11
<212> TYPE: PRT
<213> ORGANISM: Artificial sequence
<220> FEATURE:
<223> OTHER INFORMATION: synthetic polypeptide

<400> SEQUENCE: 9

Lys Ala Ser Arg Asp Ile Asp Asp Asp Leu Asn
1               5                   10
```

```
<210> SEQ ID NO 10
<211> LENGTH: 7
<212> TYPE: PRT
<213> ORGANISM: Artificial sequence
<220> FEATURE:
<223> OTHER INFORMATION: synthetic polypeptide

<400> SEQUENCE: 10

Glu Ala Thr Thr Leu Val Pro
1               5

<210> SEQ ID NO 11
<211> LENGTH: 9
<212> TYPE: PRT
<213> ORGANISM: Artificial sequence
<220> FEATURE:
<223> OTHER INFORMATION: synthetic polypeptide

<400> SEQUENCE: 11

Leu Gln His Asp Asp Val Pro Tyr Thr
1               5

<210> SEQ ID NO 12
<211> LENGTH: 11
<212> TYPE: PRT
<213> ORGANISM: Artificial sequence
<220> FEATURE:
<223> OTHER INFORMATION: synthetic polypeptide

<400> SEQUENCE: 12

Phe Ser Leu Ser Phe Ser Gly Val Gly Val Ala
1               5                   10

<210> SEQ ID NO 13
<211> LENGTH: 16
<212> TYPE: PRT
<213> ORGANISM: Artificial sequence
<220> FEATURE:
<223> OTHER INFORMATION: synthetic polypeptide

<400> SEQUENCE: 13

Leu Ile Tyr Trp Asp Asp Asp Lys Arg Tyr Ser Pro Ser Leu Lys Ser
1               5                   10                  15

<210> SEQ ID NO 14
<211> LENGTH: 11
<212> TYPE: PRT
<213> ORGANISM: Artificial sequence
<220> FEATURE:
<223> OTHER INFORMATION: synthetic polypeptide

<400> SEQUENCE: 14

Arg Glu Trp Lys Ala Phe Gly Ala Phe Asp Ile
1               5                   10

<210> SEQ ID NO 15
<211> LENGTH: 13
<212> TYPE: PRT
<213> ORGANISM: Artificial sequence
<220> FEATURE:
<223> OTHER INFORMATION: synthetic polypeptide

<400> SEQUENCE: 15

Ser Gly Ser Ser Ser Asn Ile Gly Ser Asn Thr Val Asn
1               5                   10
```

```
<210> SEQ ID NO 16
<211> LENGTH: 7
<212> TYPE: PRT
<213> ORGANISM: Artificial sequence
<220> FEATURE:
<223> OTHER INFORMATION: synthetic polypeptide

<400> SEQUENCE: 16

Asn Asn Gln Arg Pro Ser Gly
1               5

<210> SEQ ID NO 17
<211> LENGTH: 11
<212> TYPE: PRT
<213> ORGANISM: Artificial sequence
<220> FEATURE:
<223> OTHER INFORMATION: synthetic polypeptide

<400> SEQUENCE: 17

Ala Thr Trp Asp Asp Ser Leu Asn Gly Ala Val
1               5                   10

<210> SEQ ID NO 18
<211> LENGTH: 5
<212> TYPE: PRT
<213> ORGANISM: Artificial sequence
<220> FEATURE:
<223> OTHER INFORMATION: Synthetic linker

<400> SEQUENCE: 18

Gly Gly Gly Gly Ser
1               5
```